US012648879B1

(12) United States Patent

Guido-Sanz et al.

(10) Patent No.: US 12,648,879 B1
(45) Date of Patent: Jun. 9, 2026

(54) SPECTRAL-GUIDED WOUND MODELING AND THERAPEUTIC DRESSING

(71) Applicant: University of Central Florida Research Foundation, Inc., Orlando, FL (US)

(72) Inventors: Francisco Guido-Sanz, Orlando, FL (US); Mindi Anderson, Orlando, FL (US); Desiree Diaz, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 19/272,283

(22) Filed: Jul. 17, 2025

Related U.S. Application Data

(60) Provisional application No. 63/818,360, filed on Jun. 5, 2025.

(51) Int. Cl.
A61D 7/00 (2006.01)
A61D 9/00 (2006.01)
(Continued)

(52) U.S. Cl.
CPC ............ A61F 13/0283 (2013.01); A61D 7/00 (2013.01); A61D 9/00 (2013.01); B29C 64/386 (2017.08);
(Continued)

(58) Field of Classification Search
CPC .......... A61D 7/00; A61D 9/00; B29C 64/386; B33Y 50/00; B33Y 80/00; G16H 20/10; G06T 2207/30088
See application file for complete search history.

(56) References Cited

U.S. PATENT DOCUMENTS 11,801,164 B2    10/2023   Hartwell et al.
2009/0326429 A1*   12/2009   Siniaguine .......... A61F 13/0203
                                          602/48

(Continued)

OTHER PUBLICATIONS

Rossella Laurano et al. "Wound dressing products: A translational investigation from the bench to the market" 2022. pp. 182-200. Engineered Regeneration. Pisa, Italy.

(Continued)

*Primary Examiner* — Rehana Perveen
*Assistant Examiner* — John P Hocker
(74) *Attorney, Agent, or Firm* — Anton J. Hopen; Trenam Law

(57) ABSTRACT

A multispectral photonic imaging system and associated methods are disclosed for classifying wound tissue and generating customized therapeutic wound dressings. The system employs wavelength-specific optical sources and integrated image sensors to capture multispectral reflectance data from a wound, enabling computational classification of distinct tissue types such as granulation, slough, and necrosis. A three-dimensional (3D) digital model of the wound is constructed using spatial data from depth sensors. The classified 3D wound model facilitates automated design of patient-specific dressings, featuring heterogeneous regions tailored with therapeutic compounds like antimicrobial agents, analgesics, collagen scaffolds, and hydrogel matrices precisely aligned to corresponding tissue classifications. Additional imaging modalities, including thermal and ultrasound sensors, can be integrated to enhance classification accuracy and inform targeted therapeutic placement, providing a comprehensive and personalized approach to wound management for medical and veterinary applications.

27 Claims, 10 Drawing Sheets

(51) Int. Cl.

| | |
|---|---|
| *A61F 13/02* | (2006.01) |
| *B29C 64/386* | (2017.01) |
| *B33Y 50/00* | (2015.01) |
| *B33Y 80/00* | (2015.01) |
| *G05B 19/4099* | (2006.01) |
| *G06T 7/521* | (2017.01) |
| *G06T 7/80* | (2017.01) |
| *G06V 10/58* | (2022.01) |
| *G06V 10/764* | (2022.01) |
| *G06V 10/77* | (2022.01) |
| *G16H 20/10* | (2018.01) |
| *G16H 30/40* | (2018.01) |
| *G16H 50/20* | (2018.01) |
| *G16H 50/50* | (2018.01) |
| *B29L 31/00* | (2006.01) |
| *G06V 10/82* | (2022.01) |

(52) U.S. Cl.

CPC .............. *B33Y 50/00* (2014.12); *B33Y 80/00* (2014.12); *G05B 19/4099* (2013.01); *G06T 7/521* (2017.01); *G06T 7/80* (2017.01); *G06V 10/58* (2022.01); *G06V 10/764* (2022.01); *G06V 10/7715* (2022.01); *G16H 20/10* (2018.01); *G16H 30/40* (2018.01); *G16H 50/20* (2018.01); *G16H 50/50* (2018.01); *B29L 2031/753* (2013.01); *G05B 2219/32335* (2013.01); *G06T 2207/10028* (2013.01); *G06T 2207/10132* (2013.01); *G06T 2207/20081* (2013.01); *G06T 2207/20084* (2013.01); *G06T 2207/30088* (2013.01); *G06V 10/82* (2022.01); *G06V 2201/03* (2022.01)

(56) References Cited

U.S. PATENT DOCUMENTS

| | | | |
|---|---|---|---|
| 2018/0021140 A1* | 1/2018 | Angelini | C12N 5/0062 |
| | | | 623/23.72 |
| 2022/0117794 A1 | 4/2022 | Hartwell et al. | |
| 2022/0217287 A1* | 7/2022 | Adiri | A61B 5/4833 |
| 2024/0027417 A1* | 1/2024 | Vasefi | G01N 33/12 |
| 2024/0281966 A1* | 8/2024 | Fan | A61B 5/0075 |
| 2024/0374257 A1* | 11/2024 | Desvigne | A61L 15/40 |
| 2024/0389931 A1* | 11/2024 | Strasfeld | A61B 5/443 |
| 2025/0057470 A1 | 2/2025 | Guido-Sanz et al. | |

OTHER PUBLICATIONS

Zaid Muwaffak et al. "Patient-specific 3D scanned and 3D printed antimicrobial polycaprolactone wound dressings" 2017. pp. 161-170. International Journal of Pharmaceutics. London.

Suzanne O'Callaghan et al. "'Smart Dressings' for Advanced Woundcare: A Review" Jul. 27, 2020. pp. 1-16. Journal of Wound Care. Ireland.

Jia Heng Teoh et al. "Fabricating scalable, personalized wound dressings with customizable drug loadings via 3D printing" 2022. pp. 80-94. Journal of Controlled Release. Singapore.

Jia Heng Teoh et al. "3D Printing Personalized, Photocrosslinkable Hydrogel Wound Dressings for the Treatment of Thermal Burns" 2021. pp. 1-17. Advanced Functional Materials. Singapore.

\* cited by examiner

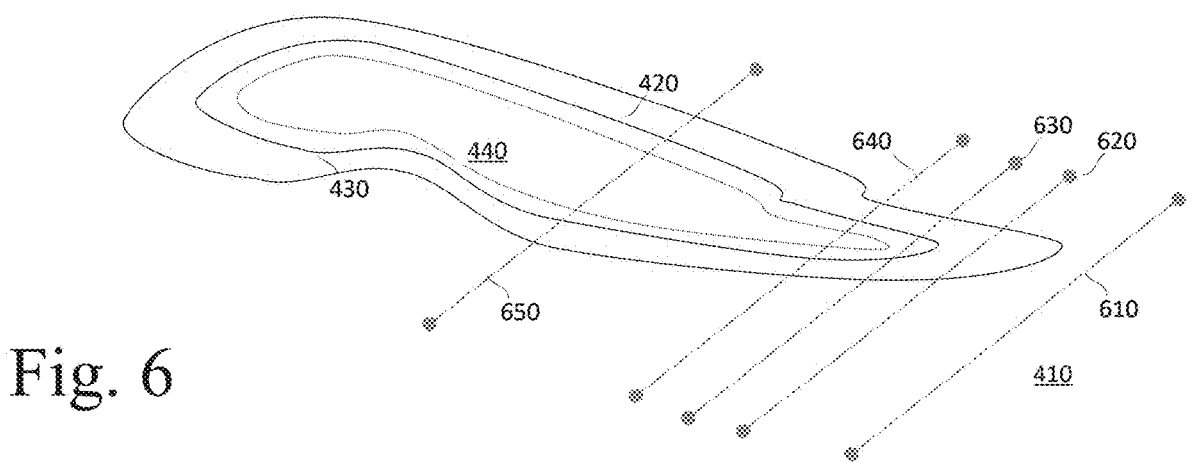
Fig. 6
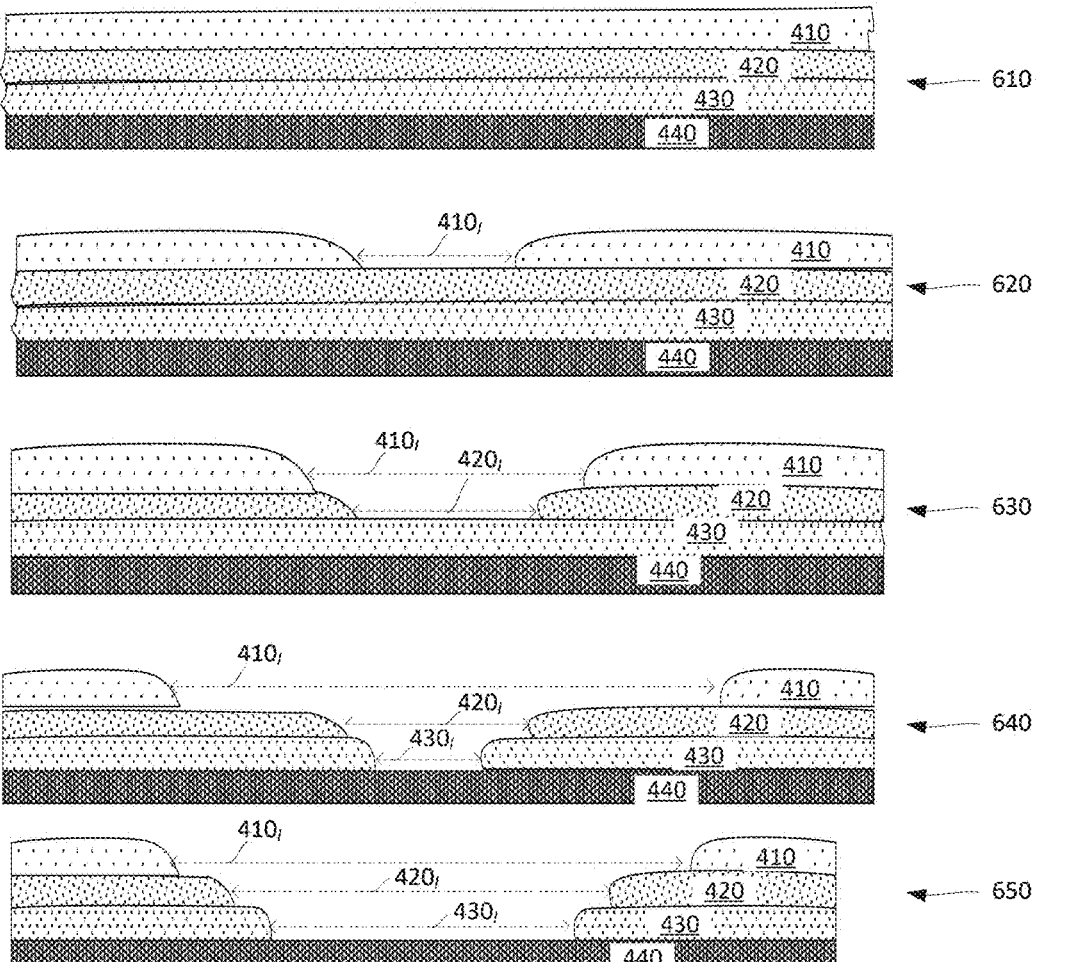

Week 1

Week 2

Week 3

SPECTRAL-GUIDED WOUND MODELING AND THERAPEUTIC DRESSING

PRIORITY INFORMATION

This nonprovisional application is a continuation of and claims priority to Provisional Application No. 63/818,360, entitled "Spectral-Guided Wound Modeling and Therapeutic Dressing," filed Jun. 5, 2025, by the same inventors.

FIELD OF INVENTION

This invention relates generally to medical imaging and wound care management systems. More specifically, the invention is a method and system to classify wound tissue types using multispectral imaging and depth sensing techniques, and to automatically generate customized therapeutic dressings featuring heterogeneous regions precisely tailored with therapeutic compounds aligned to classified wound tissues.

BACKGROUND OF THE INVENTION

Chronic wounds and complex skin injuries present significant challenges in clinical care. Accurate assessment of wound condition, including the area, depth, and types of tissue present in the wound bed, is critical for determining appropriate treatment. Traditionally, clinicians evaluate wounds using manual measurements (e.g., ruler for dimensions and cotton tipped applicator for depth) and visual inspection to estimate the proportions of tissue types such as granulation tissue, necrotic (dead) tissue, fibrinous slough, and epithelialization. This conventional approach is subjective and can vary between observers, leading to inconsistent documentation of wound status.

There is a need for more objective and quantitative wound assessment tools. Recent advances in imaging technology have introduced three-dimensional (3D) wound measurement systems. These systems use techniques like stereophotogrammetry or structured light scanning to capture the wound's surface topology, enabling accurate calculations of wound area, volume, and depth. Such 3D imaging tools improve upon flat 2D photography by accounting for irregular shapes and providing volumetric data that correlates with healing progress.

However, existing 3D wound imaging systems typically rely on standard color photographs (red-green-blue imaging) and do not perform detailed spectral analysis of tissue. They often lack the capability to automatically distinguish tissue types beyond what can be inferred from visible color and are limited to geometric measurements and basic color-based segmentation. Multispectral and hyperspectral imaging (HSI) have emerged in medical research as powerful techniques to analyze tissue characteristics by capturing reflectance across many wavelengths.

In the context of wound care, spectral imaging can non-invasively assess physiological parameters of tissues. For example, optical signatures can reveal oxygenation levels, hemoglobin concentration, water content, and even indicators of bacterial presence in wounds. The main biological factors influencing wound reflectance spectra include the amount of hemoglobin (related to blood perfusion), tissue oxygen saturation, water or edema in tissues, and melanin content of the skin. By measuring these factors, hyperspectral imaging systems can generate tissue oxygenation maps and other functional images that provide insight into wound viability and healing potential. No safety concerns have been reported in studies using such optical methods, indicating that multispectral imaging is a safe, label-free technique for clinical use.

Despite this promise, current wound imaging practices have not fully integrated multispectral analysis into routine assessment. Prior art systems have generally lacked the combination of high-fidelity 3D wound modeling and true multispectral tissue analysis in a single integrated solution. In particular, no existing commercial wound assessment device provides both precise 3D morphology capture and detailed spectral classification of wound tissue composition. As a result, clinicians still often rely on separate tools or subjective visual inspection to determine tissue health within a wound.

Another area of need in wound management is personalized treatment. Once a wound is assessed, choosing or designing an optimal dressing or therapy is the next step. Traditional wound dressings are generic pads or bandages that may not perfectly conform to an individual's wound shape, and they provide uniform treatment across the wound. Advances in biomaterials and 3D printing have opened the door to customized wound dressings that can be tailored to a patient's specific wound geometry and needs. Researchers have demonstrated the fabrication of custom-fit wound dressings (for example, using hydrogel materials) by first 3D scanning the patient's anatomy and then 3D printing a dressing that matches the contours of the wound area. These precision-fitted dressings ensure good contact with the wound bed, which can improve healing by maintaining appropriate moisture and delivering medications directly where needed. For instance, custom 3D-printed hydrogel dressings have shown enhanced healing in preclinical models by promoting tissue regeneration and controlling infection.

Despite these advances, the design of such tailored dressings is not yet automated in clinical practice and typically requires separate scanning and manufacturing steps. Accordingly, there is a need for an integrated system that not only measures wound dimensions but also identifies the types of tissue present, to inform targeted therapy. Ideally, such a system would combine multispectral photonic imaging (for tissue characterization) with 3D modeling (for shape measurement), and use the resulting data to automatically plan or fabricate a personalized therapeutic dressing. Integration of additional modalities such as thermal imaging could provide further context (e.g., highlighting areas of inflammation or infection through elevated temperature), and ultrasound imaging could supply information on subsurface structures or wound depth beyond what optical methods can capture. The present invention addresses these needs by providing a comprehensive wound assessment and treatment planning system that improves upon prior art 3D wound scanners through the novel incorporation of spectral tissue analysis and advanced data integration.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The present invention is directed to a multispectral photonic wound tissue classification system that combines advanced imaging hardware and software to assess wounds and facilitate customized treatment. In one aspect, the invention provides a system for capturing and analyzing multispectral images of a wound to automatically classify different tissue types present in the wound bed. The system comprises an imaging apparatus with photonic (light-based) sensors configured to capture reflected light from the wound across multiple distinct wavelength bands (for example, across visible and infrared spectra). By analyzing the intensity and spectral signatures of the reflected light, the system distinguishes tissue characteristics such as oxygenated versus non-oxygenated tissue, or healthy granulation tissue versus necrotic tissue. This multispectral analysis yields a tissue classification map indicating the distribution of tissue types within the wound.

In another aspect, the invention includes a method for generating a three-dimensional model of the wound area in conjunction with the spectral data. The imaging apparatus may incorporate or coordinate with a depth-sensing mechanism (such as stereo cameras, structured light projector, or time-of-flight sensor) to capture the topography of the wound. The result is a 3D digital reconstruction of the wound surface. The tissue classification map obtained from multispectral analysis can be mapped onto this 3D reconstruction, creating a rich model of the wound that contains both geometric and tissue-composition information. The system's software can quantify parameters from this model, such as wound volume, area of each tissue type, and depth of tissue layers, providing clinicians with objective metrics.

A further aspect of the invention is the use of the classified 3D wound model to design a patient-specific therapeutic wound dressing. Based on the wound's shape and the identified tissue distribution, the system generates a dressing design tailored to the wound. In embodiments, the dressing design is a 3D printable structure that conforms exactly to the wound's geometry (filling crevices and accommodating protrusions) and can be fabricated from biocompatible materials.

Optionally, the system can incorporate rules or algorithms to adjust the dressing's properties in different regions according to the underlying tissue classification. For example, making certain areas of the dressing more absorbent where exudate is detected, or embedding antimicrobial agents in regions overlying necrotic tissue. The invention may output the dressing design to a connected 3D printer or other fabrication apparatus, thus enabling on-demand creation of the custom dressing in a clinical setting.

In some embodiments, the multispectral imaging system is augmented with additional sensors to improve classification accuracy and broaden the diagnostic capabilities. A thermal imaging sensor (infrared camera) can be integrated to capture the temperature distribution of the wound and surrounding skin. Thermal data helps identify hotspots that could indicate infection or inflammation, and cooler areas that might indicate poor blood flow. An ultrasound module can also be included or used in tandem; by emitting ultrasound and capturing the echo signals, the system can probe beneath the visible surface of the wound to determine the thickness of tissue layers or the presence of underlying features (such as fluid pockets or exposed bone). Data from the ultrasound can be combined with the optical 3D model to more accurately represent the wound depth and internal structure. The integration of multi-modal data (optical spectral, thermal, and ultrasound) provides a more comprehensive assessment than any modality alone.

The system's software leverages advances in artificial intelligence (AI) for image analysis. In particular, a trained machine learning model (for example, a deep neural network) may be employed to perform segmentation of the wound in the images and classification of tissue types. The AI model can be trained on a large database of wound images where regions have been labeled by experts as granulation, slough, necrosis, epithelial tissue, etc. Using this learned knowledge, the model in the device can analyze new wound images and produce an accurate segmentation map, even in challenging cases or varying lighting conditions. The inclusion of multispectral data enhances the model's ability to differentiate tissues that might appear similar in standard color images. For example, slough (yellowish fibrin) and adipose tissue might be hard to distinguish under visible light, but their spectral reflectance profiles differ in certain infrared bands, aiding classification. The AI-assisted segmentation can also delineate the wound boundaries (separating wound from normal skin) and even identify different skin layers or degrees of tissue damage, which is useful for assessing wound severity.

The invention is applicable to both human and veterinary medicine. In one embodiment, the system is used for chronic wound care in human patients (such as diabetic ulcers, pressure ulcers, or venous ulcers), providing consistent documentation of healing progress and alerting clinicians to changes (like emerging necrotic areas or infection). In another embodiment, the system is adapted for use in animals, for example, in equine or canine wound management. Animal wounds can be difficult to assess due to fur and variations in anatomy; the multispectral approach, possibly after shaving the area, can similarly classify tissue health in veterinary wounds. The system can account for species-specific skin characteristics through calibration settings or training data. Additionally, beyond open wounds, the system can be utilized for dermatological assessments of skin abnormalities that are not open wounds. For instance, it could be used to analyze burn injuries (determining burn depth and severity by spectral signature), to examine suspicious skin lesions or ulcers, or to monitor dermatologic conditions like infections or inflammatory lesions. The spectral and AI-based tissue analysis provides objective data that could assist in diagnosing and treating these skin conditions.

The invention provides a method for classifying wound tissue and generating customized therapeutic wound dressings. Initially, the wound on a subject is illuminated using an imaging apparatus with multiple optical sources, each emitting distinct wavelengths of light. A spatially aligned image sensor captures a set of multispectral images corresponding to these emitted wavelengths, generating a tangible multispectral dataset reflecting tissue-specific differences in optical reflectance. A trained machine-learning classification algorithm stored in non-transitory memory processes this dataset to spatially classify distinct tissue types such as granulation, slough, or necrotic tissues, producing a detailed wound tissue classification map. Concurrently, depth data is collected using a structured-light or time-of-flight depth sensor integrated with the imaging apparatus, creating a three-dimensional digital surface model of the wound area. Leveraging both the classification map and the 3D digital model, a processor automatically generates a digital fabrication file, which includes instructions tailored for a three-dimensional printer. This fabrication file defines the precise geometry of a patient-specific wound dressing, customized to match the spatial geometry and tissue-type distribution of the wound. The dressing geometry further includes variable physical or chemical properties explicitly based on the identified tissue types at corresponding spatial locations. This digital fabrication file is then transmitted to a computer-controlled 3D printer, fabricating the patient-specific therapeutic wound dressing as a tangible medical product customized precisely for the individual wound characteristics.

The optical sources mentioned include wavelength-specific light-emitting diodes (LEDs) that emit visible and infrared spectra. The machine-learning classification algorithm utilized in the process can specifically be a convolutional neural network that has been pre-trained on labeled wound tissue datasets. In some implementations, additional thermal imaging data from an infrared thermal sensor integrated with the imaging apparatus further enhances the accuracy of tissue classification. Moreover, ultrasound imaging data from an ultrasound transducer, integrated with or coupled to the imaging apparatus, can also be incorporated into the 3D digital surface model to improve spatial accuracy in characterizing sub-surface tissues. Additionally, the algorithm adjusts dynamically to baseline skin pigmentation measured from tissue adjacent to the wound, refining classification thresholds to accommodate varying skin tones accurately.

The invention further encompasses that the customized wound dressing specifically includes regions with antimicrobial materials strategically positioned directly over areas classified as necrotic tissue. Significantly, the customized dressing is not uniform but rather includes multiple heterogeneous regions, each region containing distinct therapeutic compounds specifically selected based on the classified tissue type and condition beneath it. These therapeutic compounds may include antimicrobial agents, analgesics, collagen scaffolds, hydrogel matrices, anti-inflammatory agents, growth factors, or enzymatic debridement agents. The therapeutic compounds in the dressing are strategically localized in distinct vertical layers, determined by the depth at which specific tissue types have been identified within the wound. Moreover, these therapeutic compounds can also vary laterally across the dressing, specifically targeting tissue conditions at distinct spatial coordinates identified during the wound assessment. Additionally, the described method can be applied not only to human subjects but also to non-human animals, with the imaging apparatus calibrated specifically to accommodate optical properties related to the skin or fur of animals.

Correspondingly, the invention provides a multispectral wound tissue classification and dressing fabrication system. This system includes an imaging apparatus comprising multiple wavelength-specific optical emitters to illuminate the wound and at least one image sensor spatially aligned with these emitters to capture multispectral images. A depth sensor is included to provide comprehensive 3D spatial data of the wound. A processing unit, containing at least one processor and non-transitory computer-readable memory, stores instructions to process multispectral image data and depth data, classify wound tissue types using machine-learning algorithms, generate a three-dimensional wound surface model, and create a digital fabrication file defining a customized dressing that matches both the wound surface and classified tissue characteristics. A computer-controlled three-dimensional printer fabricates the customized dressing according to this digital fabrication file. Optionally, an infrared thermal imaging sensor and ultrasound transducer may also be integrated into this system, enhancing classification and subsurface characterization. The customized dressing produced by this system distinctly features therapeutic regions tailored specifically from antimicrobial, analgesic, collagen scaffold, or hydrogel materials based explicitly on the underlying tissue type and condition identified during imaging.

Finally, the invention encompasses a non-transitory computer-readable medium storing executable instructions. When executed by a processor, these instructions enable a system to perform wound tissue classification and customized dressing creation. The method steps include receiving multispectral image data captured under multiple predetermined optical wavelengths, classifying wound tissue types via trained machine-learning models based on reflectance characteristics, and generating a 3D wound surface model from depth sensor data. The instructions further automate the design of a customized wound dressing digital file, explicitly incorporating heterogeneous therapeutic regions precisely aligned with classified tissue types and conditions. The digital file is then transmitted to a three-dimensional printer, which fabricates the tangible customized therapeutic wound dressing. Additional instructions may integrate thermal and ultrasound imaging data into the tissue classification and 3D wound model creation processes and dynamically adjust classification algorithms based on adjacent skin pigmentation measurements. The therapeutic compounds used in these customized dressings may include antimicrobial agents, analgesics, collagen scaffolds, hydrogel matrices, anti-inflammatory agents, growth factors, or enzymatic debridement agents, strategically localized to target specific wound tissue classifications effectively.

These and other important objects, advantages, and features of the invention will become clear as this disclosure proceeds. The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 6 is an illustrative diagram of taking slice topographies of the wound for 3D modeling.

DETAILED DESCRIPTION OF THE INVENTION

System Overview and Architecture

Figure 1:
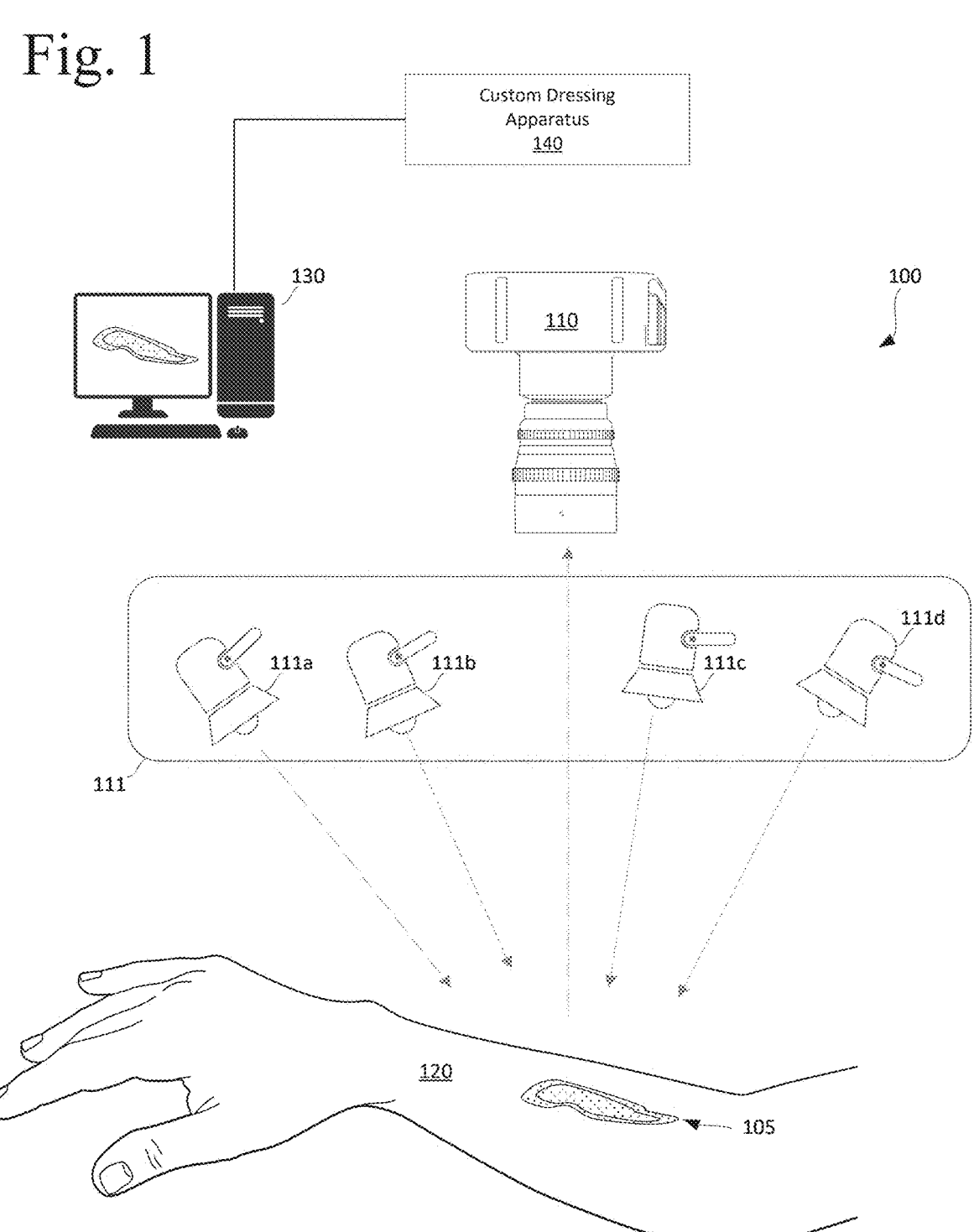
FIG. 1 is a diagrammatic view of the invention showing multispectral illumination and imaging of a wound.

Referring to FIG. 1, an exemplary multispectral photonic wound tissue classification system (shown generally as system 100) is depicted. The system 100 integrates hardware and software components for wound imaging, data analysis, and custom dressing fabrication. In the illustrated embodiment, the system 100 comprises a multispectral imaging assembly, various supplemental sensors, a computing system, and a custom dressing fabrication device. Specifically, the imaging assembly includes an image sensor 110 (e.g., a digital camera or specialized multispectral sensor) and a set of multispectral light sources 111 (illustrated as elements 111*a*, 111*b*, 111*c*, 111*d* in FIG. 1). The light sources 111*a*-111*d* are arranged to illuminate a wound site 105 on the arm 120 of a patient from multiple angles and at different wavelengths. In one embodiment, each light source emits a distinct narrow spectral band (for example, source 111*a* emitting around 450 nm, 111*b* around 550 nm, 111*c* around 660 nm, and 111*d* around 850 nm, as later shown in FIG. 3). This configuration provides controlled lighting in the visible and near-infrared ranges to capture multispectral reflectance data from the wound 105. The light sources 111*a*-111*d* may be high-intensity LEDs or laser diodes with known spectral outputs, and they can be fired sequentially or in patterns to illuminate the wound 105.

The image sensor 110 is positioned to receive light reflected from the wound 105. In the example of FIG. 1, the image sensor 110 is coupled with appropriate optics (such as lens assemblies and optical filters) to capture high-resolution images of the wound under each illumination condition. The image sensor 110 may be sensitive across the combined spectral range of the light sources, or may include multiple sensors (or a single sensor with multiple filter channels) to separately record different wavelength bands. The imaging assembly (110 and 111*a*-111*d*) is arranged such that the wound region is imaged with uniform coverage by each spectral band. In some embodiments, the light sources 111*a*-111*d* are arranged around the sensor 110 (for example, in a ring or an array) to minimize shadows and to allow multi-angle illumination. By varying the angle of incidence of illumination (as suggested by the angular placement of sources in FIG. 1), the system can capture not only spectral reflectance differences but also surface contour information via photometric techniques. For instance, sequential images lit from different directions can be analyzed to deduce surface normals or depth variations of the wound 105, contributing to three-dimensional shape reconstruction as described later.

In addition to the optical imaging components, the system can include ultrasonic and thermal sensors for complementary data acquisition. In the embodiment of FIG. 1, an ultrasound sensor is positioned at the wound site 105. The ultrasound sensor may be a high-frequency ultrasonic transducer or an array of transducers placed in contact with or adjacent to the wound 105. This sensor is used to measure subsurface structure and depth of the wound. For example, the ultrasound sensor can emit acoustic pulses and receive echoes to determine the depth profile of the wound bed and the thickness of various tissue layers in different regions. The output of ultrasound sensor provides quantitative depth measurements (e.g., maximum wound depth, presence of undermining or cavities) that supplement the surface imaging data. The system may also include a thermal imaging sensor (not explicitly shown in FIG. 1) such as an infrared camera or IR thermometer integrated into the imaging assembly 110 or provided as a separate unit. The thermal sensor captures temperature distribution across the wound 105 and surrounding tissue, identifying regions of inflammation or poor perfusion via temperature variations. Both the ultrasound data and thermal data are fed into the central computing system 130 for analysis alongside the optical images. By integrating multispectral optical imaging with ultrasound and thermal sensing, the system obtains a rich set of multimodal data describing the wound's external appearance, internal depth profile, and physiological state.

The various sensor and imaging components communicate with a computing system 130 (shown in FIG. 1 as a computer or processing unit). The computing system 130 can be a dedicated microprocessor or FPGA within a portable device, or an external computer workstation, or a cloud-linked computing device, depending on the implementation. It includes memory for storing captured data (images, sensor readings) and software modules for processing the data as will be detailed. The computing system 130 is operatively connected (via wired or wireless link) to both the imaging assembly (110, 111, etc.) and to a custom dressing fabrication apparatus 140. The custom dressing fabrication apparatus 140 (seen in FIG. 1 and later illustrated in FIG. 7) is a device configured to manufacture a wound dressing based on the data and design provided by the computing system 130. In one preferred embodiment, the apparatus 140 is a 3D fabrication device such as a multi-material 3D printer capable of depositing or forming layers of biocompatible material. It may include a movable print head, cartridges or reservoirs for different dressing materials (e.g., hydrogel, polymer, therapeutic compounds), and a control interface to receive fabrication instructions from computing system 130. The apparatus 140 can be co-located with the imaging system for immediate on-site dressing production (for example, as part of a portable unit or a cart in a clinical setting), or it can be a separate unit that receives the design remotely.

Overall, the system's hardware components are integrated such that after imaging a wound and analyzing its condition, a patient-specific wound dressing can be designed and fabricated in a closed-loop manner. The arrows and connections in FIG. 1 conceptually indicate this integration: the computing system 130 collects data from image sensor 110 (and lights 111*a*-111*d*), processes it, and then controls the dressing fabrication device 140 to produce a custom dressing 810 (as will be described with reference to FIGS. 7, 8A and 8B). The following sections describe in detail the workflows and operations of the system, referencing the enumerated process steps shown in FIG. 2 and the various data representations illustrated in FIGS. 3-8B.

Multispectral Imaging and Data Acquisition

Figure 2:
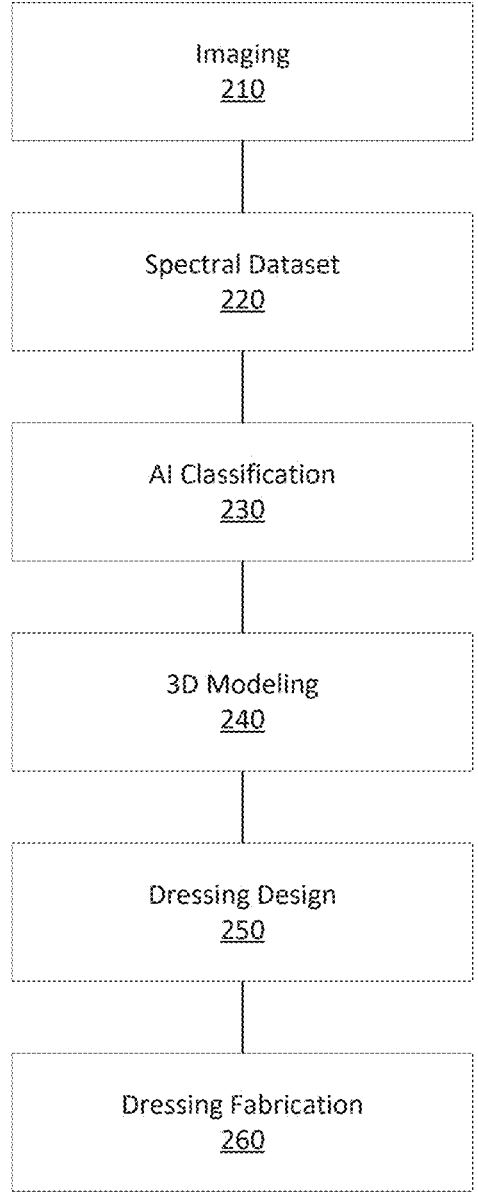
FIG. 2 is a flow chart diagram of the imaging, classification modeling and wound dressing process.

The process begins with an imaging step 210 as shown in the workflow diagram of FIG. 2. In this step, the wound 105 is illuminated and imaged using the multispectral assembly described above. The goal of imaging step 210 is to capture a comprehensive set of data that characterizes the wound's appearance under different spectral conditions, forming a spectral dataset 220 for analysis.

Figure 3:
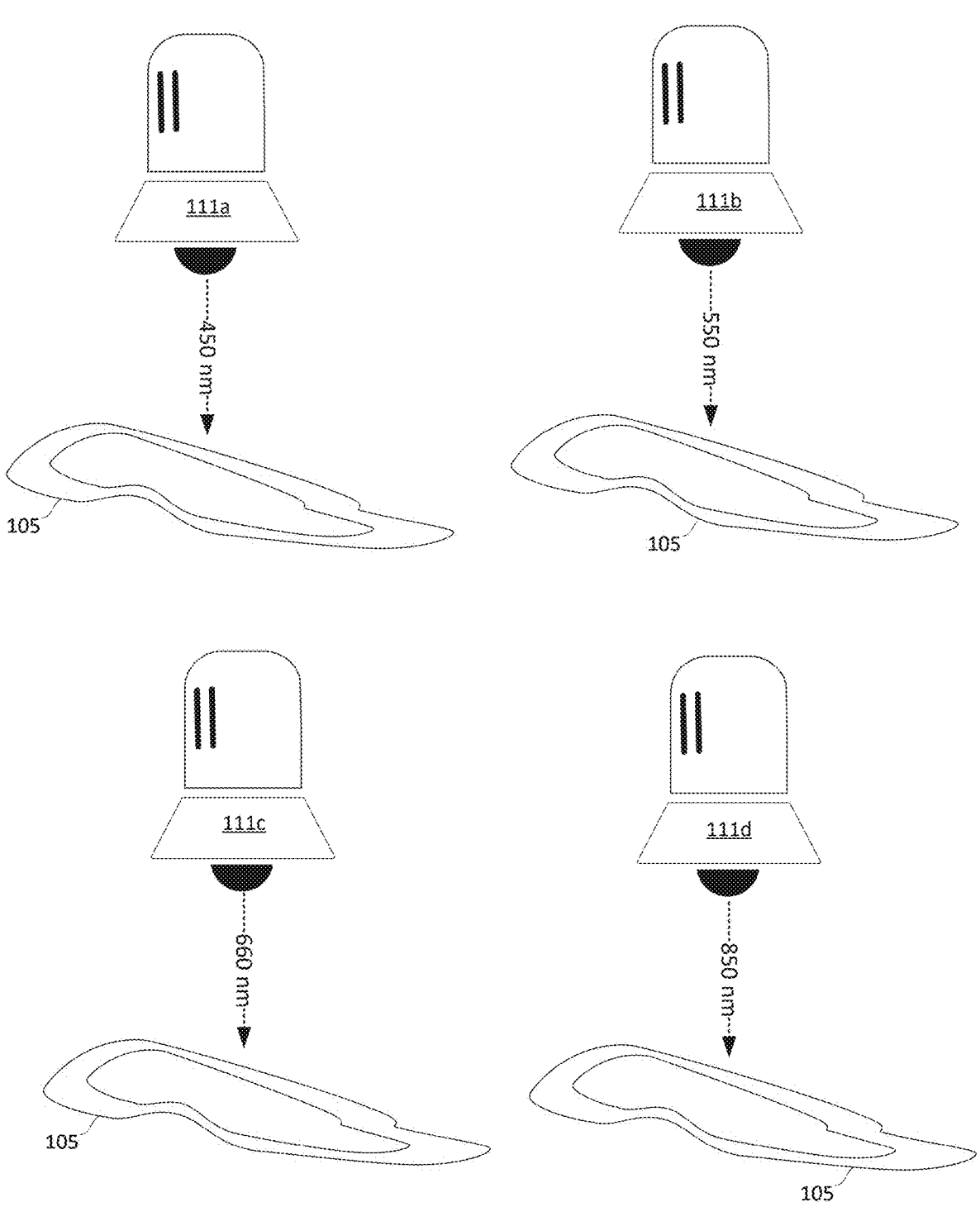
FIG. 3 shows a plurality of wavelength light sources illuminating the wound.

In one embodiment, the imaging 210 involves sequentially activating each of the light sources 111*a*-111*d* and capturing an image with sensor 110 under each illumination. This yields multiple images, each corresponding to a different wavelength band of reflected light from the wound. For example, referring to FIG. 3, four sub-figures illustrate the wound 105 as imaged under four distinct wavelengths. In FIG. 3 (top-left), the wound area 105 is illuminated by light source 111*a* (which emits, for instance, roughly 450 nm blue light), resulting in an image where certain tissue types may appear with high contrast (e.g., granulation tissue might reflect differently than necrotic tissue under blue light, causing a particular pattern or shading as indicated). In FIG. 3 (top-right), illumination by source 111*b* (e.g., green ~550 nm) produces a different contrast pattern in the wound 105. Similarly, FIG. 3 (bottom-left) shows the wound under source 111*c* (e.g., red ~660 nm), and FIG. 3 (bottom-right) under source 111*d* (e.g., near-infrared ~850 nm). Each wavelength emphasizes different chromophores and tissue characteristics: for instance, shorter wavelengths might highlight oxygenated hemoglobin distribution (useful for assessing perfusion in tissue), whereas longer near-infrared can penetrate slightly deeper and reveal sub-surface differences or moisture content. The set of images collected (one per illumination band) constitutes a multi-channel spectral dataset 220 representing the wound.

Optionally, the imaging step 210 can also include capturing a standard color image (e.g., under broad-spectrum white light or under combined illumination) for documentation and for algorithms that rely on true-color information. The system may further capture fluorescence images if fluorescent markers or endogenous fluorescence is used, for example, if certain wound bacteria produce fluorescence under ultraviolet (UV) illumination, an additional UV light source and corresponding sensor filter can be included in the imaging assembly to capture that data. These variations are all encompassed by the multispectral imaging approach.

In addition to optical images, the spectral dataset 220 can be expanded to include other spatially registered data layers. The computing system 130 can synchronize the ultrasound sensor to perform a scan either before or after the optical imaging, generating a depth map or a set of point-by-point depth measurements across the wound 105. For instance, the ultrasound probe might be moved across the wound (manually or via a mechanized actuator) to sample the depth at various coordinates, producing a matrix of depth values corresponding to the wound area. This depth map can be aligned to the image coordinate system (for example, by knowing the probe position relative to the camera or by marking key points). Likewise, if a thermal sensor is used, a thermal image of the wound can be captured, which yields a temperature map across the wound surface. These additional modalities (ultrasound depth data, thermal image) can be considered additional channels in the dataset, analogous to additional spectral bands, except they measure different physical properties (geometry and temperature rather than reflectance).

All collected data, the multispectral images, optional true-color image, depth measurements, and thermal map, are stored in memory as the wound's spectral dataset 220. In some embodiments, the dataset may be structured as a multi-dimensional matrix or "data cube" where two dimensions correspond to spatial coordinates (x, y across the wound) and the third dimension indexes the channel (different wavelengths and modalities). For example, a given pixel location in this dataset will have intensity values for 450 nm, 550 nm, 660 nm, 850 nm images, as well as a temperature value and a depth value. This rich dataset forms the input to the analysis algorithms.

To ensure accuracy, the imaging process may apply calibration procedures. Prior to or during imaging 210, the system can calibrate the sensor 110 for each wavelength (using reference targets or known reflectance standards placed near the wound) so that the captured intensities can be converted to meaningful reflectance values independent of distance or illumination variation. Additionally, if the illumination angles from 111*a*-111*d* are used to derive 3D shape, the system may perform a photometric calibration: for instance, knowing the relative positions and intensities of each source allows the computing system 130 to compute the surface normal at each point of the wound by comparing the brightness under different lights. In some embodiments, a structured light approach is used: one of the light sources could project a known pattern (e.g., a grid or stripe pattern) onto the wound, and the distortion of that pattern in the captured image reveals 3D surface information. Whether by multi-angle shading analysis or structured projection, the outcome is that along with spectral reflectance, surface topography data can be gleaned from the imaging step 210.

Thus, by the end of the data acquisition phase (steps 210 and 220 in FIG. 2), the system has acquired a comprehensive dataset characterizing the wound 105 in multiple dimensions: spectral reflectance, geometric depth, and thermal profile. This dataset 220 is now available for further processing by the computing system 130, specifically for tissue classification and wound feature extraction as described next.

Tissue Classification and Analysis

Following data acquisition, the system performs AI-driven classification 230 on the spectral dataset to identify different tissue types and relevant features within the wound 105. The computing system 130 executes software algorithms-which may include machine learning models or image processing routines—to analyze the images and sensor data and to categorize regions of the wound according to tissue composition or condition. The workflow of FIG. 2 highlights AI Classification 230 as a distinct step, indicating that an artificial intelligence or algorithmic decision module processes the spectral dataset 220 to produce a classified wound dataset.

In one embodiment, the computing system 130 utilizes a trained convolutional neural network (CNN) or similar deep learning model that has been trained on wound images labeled by tissue type. The multispectral images can be fed as multiple channels into the model, enabling the AI to leverage differences in reflectance at various wavelengths that correlate with tissue types (such as necrotic tissue vs. healthy tissue). Additionally or alternatively, classical image processing techniques and thresholding can be used in combination with machine learning. For example, the system might compute vegetation indices or color ratios (techniques borrowed from hyperspectral analysis) for each pixel, such as using the red/green reflectance ratio to highlight areas of inflammation, or detecting the presence of certain absorption features indicative of hemoglobin or melanin to distinguish new granulation tissue from surrounding skin.

The classification step 230 may output a segmentation of the wound image: essentially an annotation for each pixel or region indicating what type of tissue is present. Common tissue categories in wound analysis include (but are not limited to): necrotic tissue (dead tissue, often black or brown), slough (devitalized yellowish tissue), granulation tissue (viable new connective tissue, typically red and moist), epithelial tissue (new skin growing from the edges, pink), macerated tissue (over-hydrated, white), or healthy skin (intact tissue around the wound). The AI model can assign each image location to one of these categories. In cases of burns, classification might distinguish burn depth levels (e.g., partial thickness vs. full thickness) based on the spectral signatures. If the wound is infected, certain spectral or thermal cues (such as increased temperature or specific fluorescence from bacterial metabolites) can also be identified—the classification module could flag regions likely infected or with high bacterial load.

Figure 4:
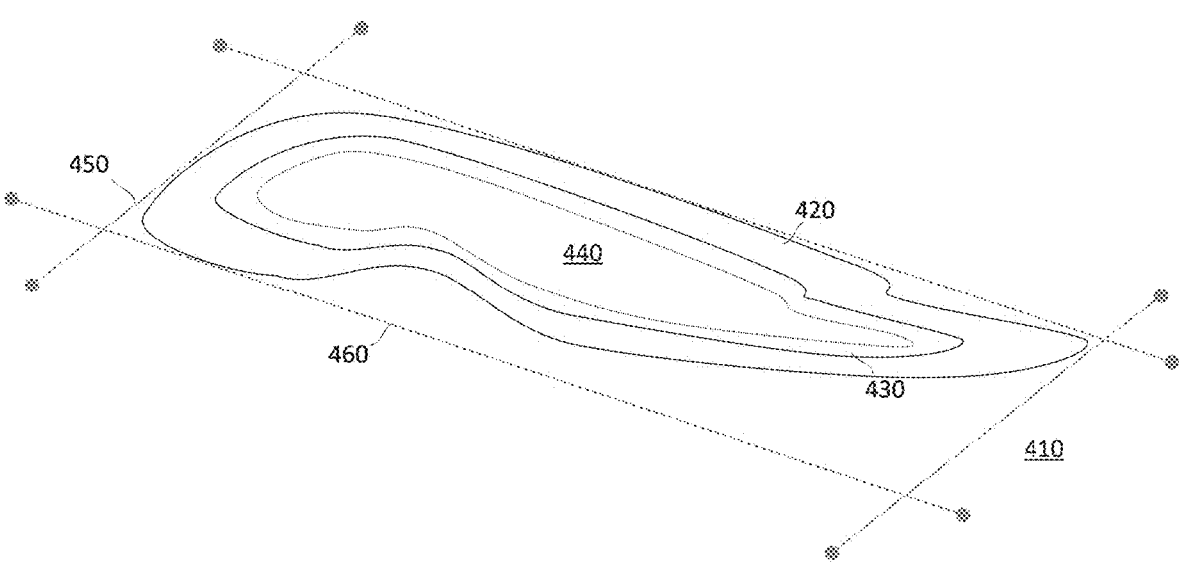
FIG. 4 is a diagrammatic view of a wound having different tissues and a coordinate dimensioning of the wound as a whole.

Referring to FIG. 4, an example output of the tissue classification is depicted in a perspective view. In this figure, the wound region has been computationally segmented into discrete areas labeled 420, 430, and 440, with 410 indicating surrounding tissue. Each of these numeric labels corresponds to a particular tissue type as determined by the analysis. For instance, region 420 could represent granulation tissue, region 430 might represent slough (fibrous exudate), and region 440 might represent necrotic tissue at the wound bed. The region labeled 410 around the wound denotes the intact skin or epithelial margin at the periphery of wound 105. FIG. 4 shows these regions in an isometric view, with different shading patterns to illustrate their extents within the wound. This illustrates that the classification result is not just a flat image segmentation, but is aware of the wound's topography (drawn as a 3D shape). The classification algorithm has thus mapped out where each tissue type lies on or within the wound surface.

The integration of ultrasound depth data enhances this classification. For example, suppose the optical analysis suggests a certain region is necrotic (based on color and lack of blood indicators); the ultrasound data at that region might show a deeper void or cavity, corroborating that tissue is missing (consistent with a necrotic crater). The AI classification 230 can fuse such information: a rule-based component might say "if reflectance spectrum indicates necrosis and ultrasound shows no underlying tissue up to a certain depth, label as deep necrotic tissue (440)". Thermal data can also feed in—an area that is much hotter than surrounding skin could be inflamed or infected; the AI may label that region accordingly or mark it as needing special treatment. In sum, the classification step synthesizes all available data to produce a detailed tissue map of the wound.

The output of the classification step 230 is stored as a classified wound dataset, which includes the segmentation mask (mapping pixels/coordinates to tissue category) and can include numeric parameters such as the area of each tissue type, the depth of each region, and any specific annotations (infection markers, etc.). These results feed into both the next step of 3D modeling (which constructs a full 3D representation with layers) and the subsequent dressing design logic (which uses the tissue map to tailor the treatment). The system may also present this classification visually to a user (for verification or record-keeping)—for instance, the computing system 130 might display an image of the wound on a monitor with colored overlays for tissue types, corresponding to FIG. 4's depiction.

It should be noted that AI Classification 230 is implemented in software or firmware on computing system 130. The program executing this step may be part of a wound analysis application that retrieves the spectral dataset 220, runs the data through algorithms, and generates output files/data structures representing the wound composition. The term "AI" is used to indicate that machine learning or knowledge-based algorithms can be employed; however, simpler embodiments might use threshold rules (for example, classifying pixels above a certain red intensity and low infrared reflectance as granulation tissue). The invention encompasses any such algorithmic means to achieve tissue identification. The key result of step 230 is a comprehensive understanding of what types of tissue exist in the wound and where they are located.

Three-Dimensional Wound Modeling

After classifying the wound's tissues, the system proceeds to construct a 3D model 240 of the wound. This step utilizes both the spatial imaging information and the classification results to generate a model that represents the wound's geometry and the distribution of tissue types within that geometry. The 3D Modeling 240 step is indicated in the FIG. 2 workflow and is further illustrated by FIGS. 5 and 6.

In one embodiment, the computing system 130 combines the surface topology data (obtained from the imaging step via photometric stereo or structured light, and/or from the ultrasound depth measurements) with the segmentation of tissue types to produce a layered 3D representation. This model can be thought of as a collection of 3D meshes or volumes: for example, a mesh representing the wound surface and wound bed, with regions labeled or textured according to tissue type. The surrounding healthy skin (region 410) forms the boundary of the wound area. Within the wound boundary, the depth at each point is known from the reconstruction data, and each point is tagged with a tissue label (from classification).

Figure 5:
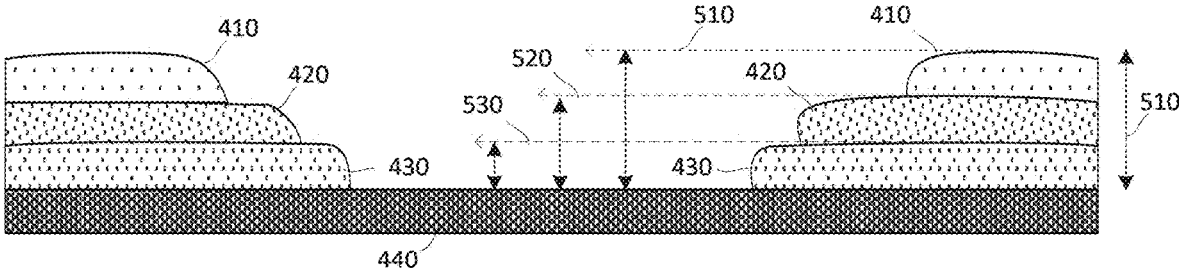
FIG. 5 is a partially sectional, elevated view of a wound showing different depths relative to the outer epidermal layer.

Referring to FIG. 5, a cross-sectional side view of an example wound model is shown. In this schematic cross-section, the different layers identified in the wound are visible: region 410 at the surface edges (epithelial tissue or skin), region 420 beneath or adjacent to it (e.g., granulation tissue forming in the wound), region 430 slightly deeper (e.g., slough or intermediate damaged tissue), and region 440 at the deepest part (e.g., wound bed or necrotic base of the wound). FIG. 5 actually shows two cross-sectional profiles side by side (representing different locations along the wound, which could correspond to, say, a left portion and a right portion of an elongated wound). The vertical dimension (depth) and horizontal dimension (width) of the wound are annotated with exemplary measurements in this figure: for instance, arrow 510 indicates a depth level dimension measurement for the rightmost profile, the maximum wound depth at that location. On the left profile, arrows 520 and 530 indicate depth measurements at two points, illustrating that the wound depth may vary across its span (one part of the wound is shallower at 520, and another part slightly deeper at 530, though both are less deep than the maximum 510 on the right side). These measurements are derived from the 3D model data: the system 130 computes distances from the skin surface 410 down to the wound bed 440 at various points. Similarly, horizontal distances or the total wound length could be measured (though not explicitly numbered in FIG. 5 aside from the conceptual 510 arrow that might also be used to denote a horizontal extent in some depiction).

Importantly, the cross-section in FIG. 5 shows how the classification layers (410, 420, 430, 440) align with depth. For example, at the far left of the wound cross-section, the top surface is healthy skin 410, below which some granulation 420 is beginning to form over a base 440. In the deeper section on the right, the surface at the edge is 410 (skin), transitioning to 420 (granulation) toward the wound center, then an area of slough 430 mid-depth, and finally a pocket of necrotic tissue 440 at the bottom. This layered depiction demonstrates that the system's 3D model captures not just a single surface, but internal composition. The 3D modeling step 240 effectively "stacks" the classification information into the third dimension using the depth data.

Referring now to FIG. 6, a more comprehensive visualization of the 3D wound model and layered tissue segmentation is provided. FIG. 6 (top) shows a perspective view of the wound (similar to FIG. 4) with multiple sectional cut lines labeled 610, 620, 630, 640, 650 across the wound's length. These lines indicate where cross-sectional slices are taken. Below the perspective view, FIG. 6 provides a series of cross-sectional side views corresponding to those cut lines 610-650. Each cross-section illustrates the profile of the wound at that specific location, with the same layer labels 410, 420, 430, 440. For example, at slice 610 (near one end of the wound), the cross-section might show a relatively shallow wound: mostly intact skin 410 with a small depression of granulation 420 and little to no slough or necrosis. At slice 630 (closer to the wound's center), a deeper depression is seen: skin 410 at the very edges, granulation tissue 420 extending a bit further in, and a noticeable region of slough 430 and necrotic base 440. By slice 650 (the other end of the wound), the profile might again change. The dashed lines and arrows within these cross-sectional images indicate the wound boundaries and depth extents at each slice. FIG. 6 shows how the wound's internal makeup varies along its length, which the 3D model captures in full detail.

The computing system 130 generates this model using software implementations of 3D reconstruction. In one embodiment, the system constructs a point cloud of the wound surface from the imaging data and then interpolates a surface mesh. The classified tissue data can be mapped onto this surface and extended downwards to the wound bed. Another approach is volumetric: create a 3D voxel grid of the wound volume (for example, using ultrasound to inform the interior). Each voxel could be assigned a tissue type label from the nearest surface classification or ultrasound reflection characteristics. The result is a voxel model where a top layer of voxels might be granulation (420) and the bottom voxels necrotic (440), etc., matching what was determined by the classification.

It is also at this stage that the system can compute quantitative wound metrics which are often important in clinical settings: volume of the wound (by integrating the area of cross-sections like those in FIG. 6), surface area of the wound opening, area of each tissue type (e.g., how many square millimeters of slough vs granulation), maximum depth (as indicated by 510 in FIG. 5), and wound circumference or perimeter. These metrics can be derived automatically from the 3D model and stored for reporting or tracking healing over time. For instance, if the patient is imaged again later, the volume reduction can be calculated by comparing the models.

The 3D Modeling 240 step is thus an integration of data into a cohesive representation. Software-wise, this may be implemented by a module in computing system 130 that takes the 2D classification maps and "drapes" them over a 3D surface. If multiple images or viewpoints were used, structure-from-motion or multi-view stereo algorithms could also be employed to get the surface geometry. However, the invention is not limited to any particular reconstruction technique; it encompasses any method of generating a representation of the wound's shape and internal composition using the acquired data. The outcome (as illustrated in FIGS. 5 and 6) is a detailed three-dimensional depiction of the wound, segmented by tissue type. This model directly informs the next stage: designing a custom therapeutic dressing tailored to this specific wound profile.

Dressing Design and Fabrication

With a complete 3D model and tissue map of the wound, the system (via computing device 130) moves to the Dressing Design 250 step of the workflow (see FIG. 2). In this step, software algorithms design a custom wound dressing based on the wound's dimensions and tissue needs. The subsequent Dressing Fabrication 260 step carries out the physical creation of this designed dressing using the custom dressing apparatus 140. Together, these steps ensure that a patient-specific therapeutic dressing is produced to optimally treat the wound 105.

Figure 7:
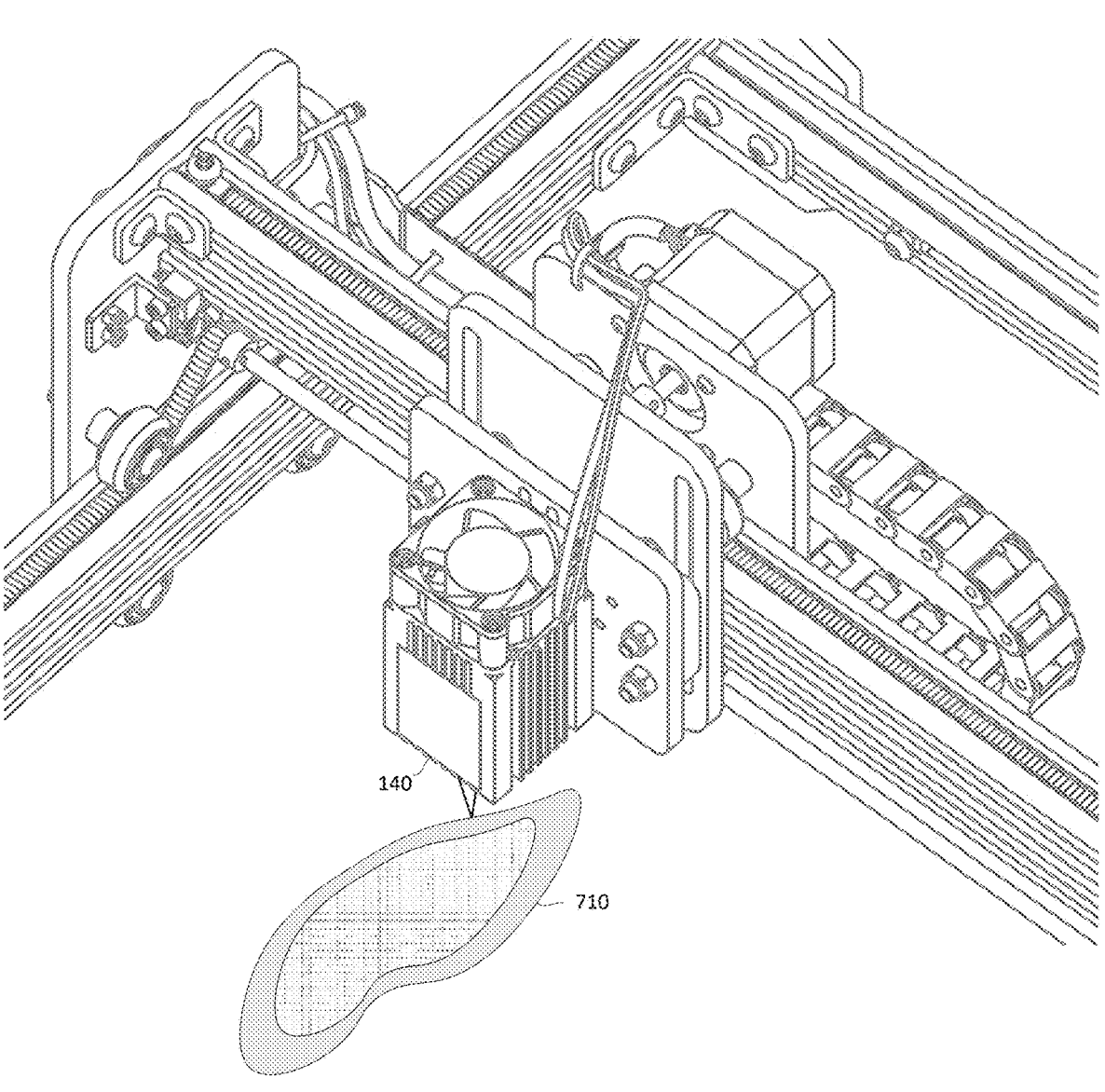
FIG. 7 is an isometric, elevated view of 3D dressing fabrication.

During Dressing Design 250, the computing system 130 determines the appropriate size, shape, and multi-layer composition of the dressing. The shape of the dressing is generally derived from the wound's geometry: for example, the outline of the dressing may match or slightly exceed the outline of the wound area as identified in the model (to ensure full coverage). The system can take the 2D projection of the wound (the area of region 105) and create a 2D pattern or stencil that covers it with some margin. This pattern can be seen in FIG. 7, where item 710 represents an example dressing outline corresponding to the wound shape. In FIG. 7, the dressing 710 is shown on the bed of the fabrication apparatus, having an irregular shape that matches a wound. The design process would have computed this shape from the model—for instance, by offsetting the wound boundary outward by a fixed safety margin (such as 5 mm) to ensure the dressing overlaps healthy skin slightly for adhesion.

Next, the design step considers layering and materials. Based on the tissue classification, the system knows which areas of the wound have which tissue type or condition (e.g., which parts are infected, which parts are deeply undermined, which parts are painful, etc.). The dressing design can include multiple layers or regions to address these conditions. For example, the system might decide that the wound needs a moisture-retentive layer over granulation tissue, an antimicrobial agent over slough or infected regions, and an absorptive filler in deep cavities. These decisions are made by a dressing planning algorithm or knowledge base, which maps wound features to treatment components.

The software may use a rules engine or AI to select components: e.g., If necrotic tissue present (440), include a debriding agent; If high bioburden suspected, include an antimicrobial; If depth >X, include a filler to support tissue growth; If patient reports high pain or wound is known painful (e.g., burns), include analgesic. These are examples of rules that could be encoded. The outcome is a specification of what the dressing will consist of, both in cross-section (layers) and in plane (regions across the area).

Figure 8A:
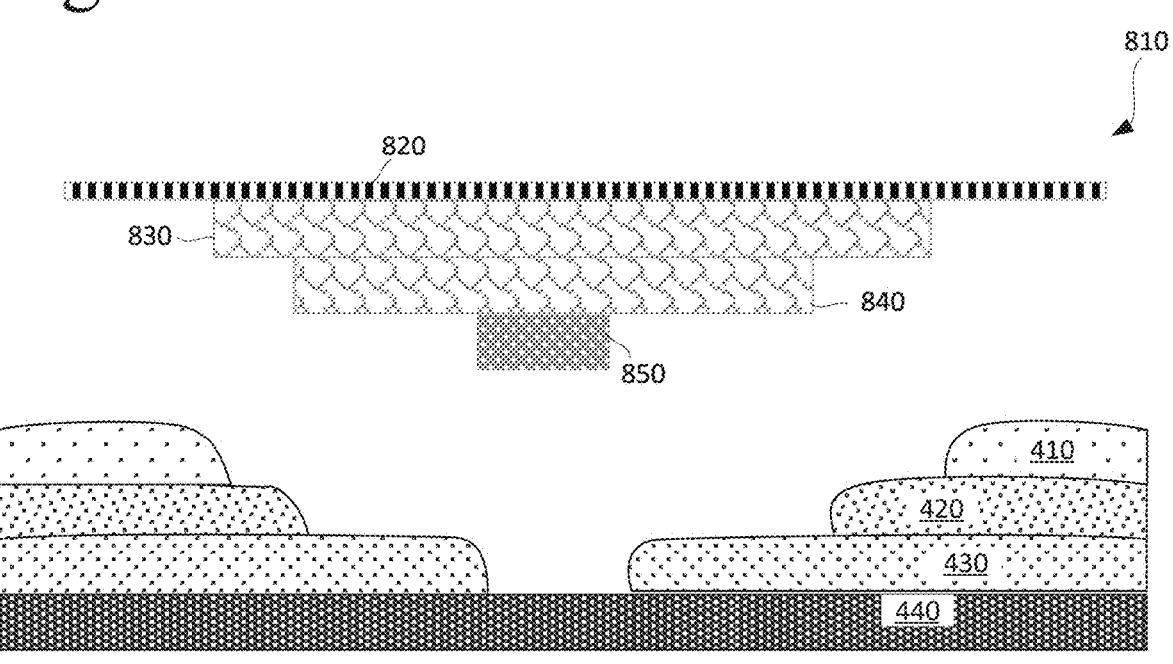
FIG. 8A is a side elevated sectional view of a 3D, custom dressing elevated over an aligned wound.
Figure 8B:
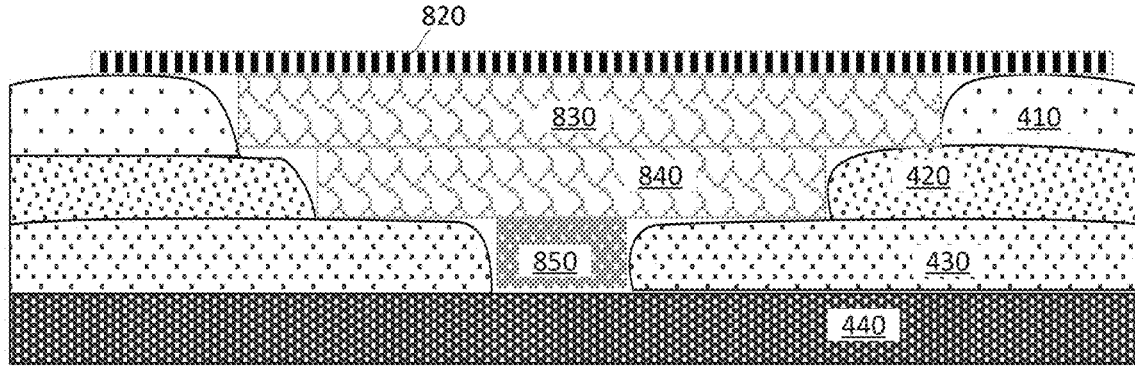
FIG. 8B is a side elevated sectional view of a 3D, custom dressing applied to the wound.

Referring to FIGS. 8A and 8B, the detailed composition of an exemplary heterogeneous dressing 810 is illustrated. FIG. 8A shows an exploded cross-sectional view (the dressing lifted above the wound), and FIG. 8B shows the dressing 810 applied on the wound cross-section. In this design, the dressing 810 comprises multiple components: a top layer 820, a first intermediate region 830, a second intermediate region 840, and a deep filler or plug 850. Each of these components is strategically placed and may contain different materials or therapeutic agents.

The top layer 820 is generally a protective cover or backing. In many designs, this could be a flexible film or adhesive layer that holds the dressing together and secures it to surrounding skin. It might be, for example, a transparent polyurethane film (common in wound dressings to provide a barrier to contamination while keeping the wound environment moist). The top layer 820 may or may not contain active agents; often it is more structural (though it could be coated with an adhesive that has antimicrobial properties as well). In FIG. 8A, 820 is shown as a thin horizontal layer spanning the entire dressing width, indicating it covers the whole wound area when applied.

Below the top layer, regions 830 and 840 represent two different materials making up the bulk of the dressing that will interface with the wound. In FIG. 8A, region 830 is drawn with a cross-hatched pattern, and region 840 with a different stipple pattern, suggesting they are distinct in composition (for example, 830 might be a lattice or foam, whereas 840 is a more solid gel or pad). These could correspond to, say, 830 being a cushion layer containing one type of medication, and 840 being another layer containing a different treatment. The figure shows these as separate blocks underneath the top layer 820, and FIG. 8B shows how they sit in relation to the wound: 830 covers one portion of the wound (like the left/central part in the illustration) and 840 covers another portion (like the right part).

The element 850 is depicted as a darker piece in the middle of the dressing, especially visible in FIG. 8B where it is nestled into a deeper pocket of the wound between the other layers. 850 likely represents a plug or filler that occupies a cavity in the wound. For example, if the wound has a deep center (as indicated by region 440 in the wound model), the design might include a correspondingly shaped filler 850 made of a material to promote tissue growth in that void. This filler could be a biodegradable scaffold or a hydrogel infused with cells or collagen that fills the dead space and encourages new tissue to form. In FIG. 8A, the filler 850 is shown below region 840 (indicating it sits deepest), and in FIG. 8B it's seen inserted into the wound base, touching the bottom (440) and the sides.

The Dressing Design 250 software would determine the shapes and extents of 830, 840, 850 based on the wound model. For instance, it might outline region 830 to correspond to where granulation tissue (420) is present-covering it with a gentle hydrogel that keeps it moist and provides growth factors. Region 840 might correspond to where slough (430) or infection is present-placing there a material containing an antimicrobial agent to help cleanse that area. Region 850 would be sized to the depth and volume of the necrotic pocket (440)—possibly containing a debriding enzyme or a collagen matrix to fill that gap. The top layer 820 is then designed to encompass all those and hold them in place, possibly extending over the edges to adhere to skin (410). Thus, the design is inherently layer-specific and coordinate-specific: each layer (vertical placement) and each position (horizontal location over the wound) is chosen deliberately according to the wound's condition as analyzed.

Once the dressing design is finalized digitally (with a CAD model or geometric representation of layers like 820, 830, 840, 850 and their compositions), the system proceeds to Dressing Fabrication 260. The computing system 130 generates control instructions for the custom dressing apparatus 140 to create the designed dressing.

As shown in FIG. 7, the custom dressing apparatus 140 is a machine that can fabricate the dressing, for example by 3D printing. In FIG. 7, the apparatus 140 has a gantry or robotic arm system typical of a 3D printer, with a print head assembly labeled 140 moving over a substrate. The print head may include multiple nozzles or a material dispenser (the figure depicts a print head with a cooling fan and a motor, suggesting an extrusion-based printer). The shape 710 on the bed is the outline of the dressing being printed, corresponding to the wound shape as discussed. The apparatus 140 builds the dressing 810 layer by layer. For instance, it may first print the deep filler 850 by dispensing a bio-ink or paste into the shape required (only in the regions needed). Then it might switch material and print the region 830 and 840 with their respective materials, possibly side by side or in a pattern that conforms to the wound area segments. Finally, it could apply or print the top layer 820 as a continuous sheet or as an impregnated mesh covering the entire area.

The fabrication device 140 is preferably equipped with multiple material capabilities to achieve this heterogeneity. For example, it could have multiple cartridges, one loaded with a hydrogel matrix material (for a moist wound healing environment, possibly used for region 830), another loaded with a collagen scaffold material (for deep filler 850), and another with an antimicrobial gel or paste (for region 840). It might also handle an adhesive polymer for the top layer 820. The computing system's instructions would include toolpaths and dispensing commands indicating where each material goes. Because the dressing is custom, the machine will deposit material only where needed—for instance, if region 830 is only on one side of the dressing, the printer will dispense that material in that zone; for region 840 another zone, etc., thus creating a map of materials across the dressing plane.

During fabrication (260), the apparatus 140 may incorporate pauses or curing steps if needed (for example, UV curing a layer, or letting a hydrogel set). The environment could be controlled (some materials might need a certain temperature or humidity to set properly). The system might also embed additional components, such as a piece of mesh or gauze, by picking and placing it-however, in many cases the entire dressing can be printed additively.

Once fabrication is complete, the result is the physical dressing 810 that mirrors the digital design. The dressing can then be applied to the patient's wound. In a practical use case, the healthcare provider could remove the dressing from the fabrication bed and immediately place it onto the wound 105, achieving a perfect fit in shape and delivering multiple therapies in the right locations.

It should be noted that the design (250) and fabrication (260) steps are generally executed automatically by the system without requiring the user to manually design the dressing. However, the system might provide an interface for a clinician to review or adjust the design before fabrication. For instance, a clinician might confirm that an antimicrobial is indeed desired in a certain area or adjust the quantity of a drug. The system could allow such inputs, then proceed to fabrication.

Heterogeneous Multi-Layer Dressing Composition and Therapeutic Agents

A key aspect of this invention is the heterogeneous dressing composition produced, meaning the dressing is not homogenous but contains different materials or medications in different portions (both across the area of the dressing and through its thickness). As illustrated in FIGS. 8A and 8B (with elements 830, 840, 850), the dressing 810 is explicitly designed to address the heterogeneity of the wound tissues. Each of these elements can carry specific therapeutic agents or have distinct physical properties optimized for the underlying tissue at that location. The result is a customized wound treatment that improves precision and efficacy compared to a one-size-fits-all dressing.

Several examples of common therapeutic agents and materials that can be incorporated into the dressing's layers are enumerated below, along with their roles and how their selective placement benefits wound healing:

Lidocaine (Local Anesthetic): Lidocaine or similar local anesthetics can be embedded in one layer of the dressing to provide targeted pain relief. For instance, an inner dressing layer (such as part of region 830 or 840) that lies against particularly sensitive areas of the wound (e.g., near nerve-rich edges or exposed nerve endings) can be infused with lidocaine. By confining the analgesic to the areas that need it, the dressing reduces pain when applied, improving patient comfort during wear and dressing changes. Coordinate-specific placement of lidocaine means that only the painful regions of the wound bed receive the anesthetic, avoiding unnecessary medication of areas that are not in pain. This targeted approach minimizes the total drug used and reduces the risk of systemic absorption. For example, if the wound edges (where new epithelium 410 is forming) are very tender, the section of the dressing covering those edges can release lidocaine locally, whereas the center of the wound (which may be less pain-sensitive if nerves were destroyed) might not receive any lidocaine.

Silver Sulfadiazine (Antimicrobial Agent): Silver sulfadiazine is a well-known topical antimicrobial, especially used in burn care to prevent and treat infection. In the custom dressing, silver sulfadiazine (or other silver-based antimicrobial such as silver nanoparticles) can be loaded into a specific region, such as 840, targeting areas of the wound that were identified as having slough or infection risk (for instance, region 430 in the wound classification). By localizing the silver compound to the sections of the dressing that contact these high-risk areas, the dressing delivers a potent antimicrobial effect exactly where needed—for example, where bacterial biofilm was detected or where tissue is necrotic and prone to infection—while not exposing the entire wound (or the patient's body) to silver. This coordinate-specific deployment helps maintain high local concentration of the antimicrobial for efficacy, and reduces potential cytotoxic effects on healthy tissue elsewhere. Silver sulfadiazine could be incorporated in a hydrogel or cream form and printed into the dressing matrix at the corresponding positions.

Hydrogel Matrices: Hydrogels (such as those made from alginate, carboxymethylcellulose, or polyacrylate polymers) are commonly used to maintain a moist wound environment, which is known to accelerate healing. In the custom dressing, a hydrogel matrix could form a layer or region (for example, making up most of 830) that lies over granulation tissue 420. Granulation tissue heals best when kept moist and insulated from desiccation. The hydrogel can slowly release moisture (or even incorporate nutrients or antibiotics) to the wound bed. Additionally, hydrogels are gentle and non-adherent, so they protect delicate new tissue when the dressing is removed. By placing a hydrogel only where needed (e.g., central wound bed), the dressing can also avoid over-moisturizing the intact skin at the periphery which could cause maceration. Thus, depth-specific placement matters: a thick hydrogel might fill a shallow depression, whereas at the very edges only a thin coating is needed.

Collagen Scaffolds: Collagen is often used in wound dressings as a scaffold to encourage tissue regeneration. A collagen dressing (often derived from bovine collagen or synthetic analogs) provides a matrix that cells can adhere to and proliferate within, effectively jump-starting the healing process in wounds that are stalled or too large to quickly fill in on their own. In this system, a collagen scaffold material can be 3D-printed as the filler 850 for deep wound cavities. For example, if the wound analysis found a deep pocket (necrotic region 440 that was debrided, leaving a cavity), the design might include a collagen sponge or foam inserted there. The 3D printer could extrude collagen or a collagen-containing bio-ink to exactly fill the void. Because the placement is guided by the wound's measured dimensions, the collagen scaffold fits perfectly, contacting the wound base and walls to provide a template for new tissue in that specific spot. Using collagen in a layer-specific way means you put it where tissue needs to regrow (depth coordinate) and not where it isn't needed (e.g., on top of intact skin, which doesn't require a scaffold). This increases effectiveness and reduces material waste.

Honey-Based Dressings: Medical-grade honey (such as Manuka honey) is known for its antimicrobial and wound-healing properties. It can help reduce infection and inflammation and promote autolytic debridement (softening and removal of dead tissue). Honey can be impregnated into a dressing material like an alginate pad or hydrogel. In the context of the custom dressing, a honey-based component might be selectively placed over regions where biofilm or slough (430) was identified. For example, region 840 could be a honey-infused alginate that will lie on an infected portion of the wound, delivering sustained antimicrobial action and aiding in debriding that section. Meanwhile, another part of the dressing covering healthy granulating areas might omit the honey to avoid unnecessary irritation. Honey is viscous, so the fabrication device might dispense it as part of a gel layer or within a mesh that holds it in place (the cross-hatched 830 region could represent a mesh soaked in honey that is printed into the dressing). The benefit of coordinate-specific honey placement is that you harness its effects exactly where needed—for instance, only on the sloughy central bed-thus optimizing the wound environment in different zones.

These examples illustrate how different therapeutic agents or functional materials can be assigned to different elements of the dressing (830, 840, 850, etc.). The system's design algorithm chooses the combination appropriate for the wound. One wound might get a lidocaine-infused hydrogel at the edges and a silver dressing in the middle; another wound might get a collagen scaffold in the base and a honey layer on top of that. The combinations are customizable.

From a layer perspective, consider the vertical stacking: The deepest layer (e.g., 850) might be a solid or foam insert primarily for structural fill and tissue growth support (like collagen or a fibrin matrix). Above that, one intermediate layer 840 might function as an antimicrobial barrier (like a sheet containing silver or iodine compound). Adjacent to it, another intermediate layer 830 might function as a hydrated gel to keep the wound moist and deliver analgesics. Finally the top layer 820 holds everything and protects from the external environment, possibly also providing oxygen permeability or vapor exchange to avoid excessive moisture accumulation. Each layer has a purpose aligned with the wound's needs at that depth. If the wound were more superficial with no deep cavity, the design might omit a deep filler like 850 and instead just have a uniform hydrogel across the wound. If the wound has varying depth (as in our example, maybe deeper in the center than the edges), the fabricated dressing 810 can have a thicker section of one material in the center and thinner towards the edges, exactly matching the contour, something pre-made dressings cannot do.

The coordinate-specific placement refers to how, across the area of the dressing, different coordinates (x,y positions corresponding to locations on the wound) receive different treatments. For example, the upper left quadrant of the dressing might contain a slow-release antibiotic because the corresponding wound quadrant was infected, whereas the lower right quadrant contains a growth factor because that area was clean but needed to epithelialize. This precise mapping ensures that each part of the wound gets a micro-environment optimized for it. Over the course of healing, this can lead to faster and more effective recovery: healthy tissue is not exposed to unnecessary drugs (which could impede cell growth if misapplied), and unhealthy tissue is more aggressively treated.

The manufacturing approach (3D printing or layering) is what enables such fine customization. Traditional dressings might combine two of these features (e.g., a collagen dressing with silver in it), but they would be uniform across the whole pad. Here, by digital fabrication, we can vary composition continuously over the dressing. For instance, the amount of silver could be higher in the center and taper off toward edges. Or the concentration of an analgesic can be higher at one side where the patient feels more pain. These gradients or discrete regions are all within scope.

The embodiments described can be varied. For example, while lidocaine, silver sulfadiazine, honey, etc., are cited, the system could similarly incorporate other therapeutic agents known in wound care: antibiotics (like gentamicin or vancomycin powder for infected wounds), antifungals (if fungal infection is an issue), growth factors (like PDGF or epidermal growth factor in a slow-release form to stimulate healing), anti-inflammatory agents (like a low-dose steroid or a non-steroidal anti-inflammatory drug (NSAID) locally to reduce excessive inflammation), debriding enzymes (such as collagenase to break down necrotic tissue), or hemostatic agents (if the wound is bleeding, materials like chitosan can be placed where bleeding is observed). The system's analysis of the wound can guide inclusion of any of these: e.g., if the wound classification noted a lot of necrotic tissue (region 440), the dressing might include an enzyme patch in that area to help debride it. The entire dressing thus becomes a composite therapeutic tool tailored to the wound.

From a structural standpoint, the dressing 810 may also incorporate physical features such as different absorptive capacities in different areas. For example, wounds often produce more exudate in certain pockets. The system can identify a location with high exudate (from the moisture content deduced or simply from known wound type) and design a portion of the dressing with higher absorbency (maybe a thicker hydrocolloid in region 840) at that spot. Conversely, a dry area would get a hydrating gel. This level of tuning improves the wound's moisture balance, which is critical in wound healing (often referred to as maintaining a "moist wound healing environment" without causing maceration of surrounding skin).

Finally, once the dressing is fabricated and applied (as in FIG. 8B), the various components 830, 840, 850 work in concert on the wound. The patient effectively receives a combination therapy, but delivered in a single integrated piece that is custom-shaped to them. This is more convenient and effective than applying multiple separate dressings or ointments. The detailed description here lays out how the system achieves that result step by step: imaging the wound in detail, analyzing what it needs, and directly manufacturing a solution. All of these elements taken together, the imaging assembly 110 with multispectral lights 111a-111d, the optional ultrasound and thermal sensing, the computing system 130 running advanced algorithms (210-240), and the fabrication device 140 making a multi-component dressing (250-260), form a cohesive system for improved wound care. Each component and step has been described in a manner consistent with how one skilled in the art might implement this invention, with the understanding that variations in hardware (for example, using a different type of sensor or printer) or in software (different algorithms or criteria for design) are possible without departing from the scope of the invention as claimed.

Predictive Wound Healing Modeling

In an embodiment of the system, the wound analysis and dressing design process are extended to model the wound's healing trajectory over time. Rather than producing a single dressing for the wound's current state, the system employs a predictive wound healing model that forecasts how the wound's topography and tissue composition will change as healing progresses. This model uses the initial multispectral classification data and three-dimensional wound geometry as a baseline, and projects forward to anticipate wound evolution at future intervals.

By analyzing known patterns of healing, for example, reduction in wound area, increase in granulation tissue, contraction of wound edges, and changes in tissue type distributions, the system can simulate one or more future wound states. The output of this predictive modeling is a series of anticipated wound conditions at specified future times or healing stages. Each predicted wound state includes details such as expected wound dimensions (area and depth reduction), the likely composition of tissues (e.g., proportion of granulation tissue vs. remaining slough or necrosis), and other features like moisture level or perfusion changes if those can be inferred. This forward-looking capability transforms the wound care process from a reactive approach (dressing the wound as it is today) to a proactive approach in which upcoming needs are forecast.

The multi-stage predictive wound model may be data-driven, having been trained on large wound healing datasets, or it may incorporate known clinical healing rate formulas and staging criteria to refine its predictions. In operation, once the system captures the current wound data, the predictive model generates a timeline of predicted wound states, effectively creating a virtual healing progression unique to the patient's wound. These predictions account for the wound type and healing intention (as discussed above) and can be adjusted to reflect expected care interventions (for instance, if debridement or additional treatments are planned, the model can incorporate those effects). The result of this modeling step is a set of anticipated wound profiles at future points in time (for example, one week from the initial scan, two weeks out, etc., depending on the clinical scenario), which then serve as targets for designing future dressings.

Time-Sequential Custom Dressing Design

Using the predicted wound states generated by the model, the system automatically designs a time-sequence of custom dressings corresponding to each stage of healing. For each anticipated future wound state, the processing unit creates a digital fabrication file (or an analogous design specification) defining a wound dressing tailored to that state. In essence, the invention produces not just one dressing, but a series of dressings, each customized to a different point along the wound's healing timeline. The first dressing in the series addresses the wound's immediate needs (as determined by the initial imaging and classification), while subsequent dressings are pre-designed for the wound conditions expected at later times. Each dressing design accounts for changes in wound size, depth, and tissue composition.

For example, if the model predicts that in seven days the wound will have contracted significantly with a predominance of healthy granulation tissue at the base, the second dressing's geometry will be correspondingly smaller, and its composition will shift towards materials that support new tissue growth rather than aggressive debridement. Likewise, if an even later stage predicts the wound nearly closed with mostly epithelial tissue forming, a subsequent dressing might be simpler, primarily a protective layer to guard the fragile new skin. All these dressing designs are generated in advance, forming a time-staged therapeutic regimen encoded in multiple digital fabrication files.

Each file carries instructions for a dressing shape and internal structure that matches the forecasted wound surface at a particular stage, as well as specifications for regionally applied compounds or varying materials suited to that stage's needs. This approach ensures that as the wound progresses through stages of healing, the patient will have on hand a dressing that fits that stage, effectively a "healing itinerary" of custom dressings. The dressings are designed as a coordinated set, often referred to as a sequential dressing kit, with each dressing numbered or otherwise identified for a specific order of use. The design process considers not only individual dressings in isolation, but also the transition between stages: for instance, the overlap in design ensures that dressing number 2 picks up where dressing number 1 left off, in terms of wound coverage and therapeutic function, so there are no gaps in care as the wound changes.

Fabrication of Staged Dressings and Packaging

Once the sequential dressing designs are finalized, the system proceeds to fabricate the series of dressings, typically in a single, coordinated production run. The fabrication apparatus (3D printer) can manufacture all the planned dressings one after the other, or simultaneously if it has multiple print heads or an array of print platforms, ensuring that the full set of stage-specific dressings is prepared together under consistent conditions.

Each dressing is created according to its respective digital file, using the appropriate materials and embedding the specified therapeutic agents in the correct regions. The output of this process is a set of custom dressings each corresponding to a different future point in the wound's healing process. These dressings are preferably produced under sterile conditions and immediately readied for use or storage. In one embodiment, the system includes or is coupled to a packaging unit that organizes the dressings into a sterile kit. For example, the dressings can be sealed in individual sterile pouches and then collectively packaged in a single box or tray that denotes the sequence of application. Each dressing is distinctly labeled to indicate when or in what order it should be used. This labeling can be numeric (e.g., "Dressing 1", "Dressing 2", "Dressing 3", corresponding to first week, second week, third week), chronological (with an expected date or time frame of application based on the model's predictions, such as "Week 1", "Week 2", etc.), or descriptive of the wound stage (for instance, "Initial-high antimicrobial", "Granulation phase support", "Epithelialization cover").

In some versions of the system, the packaging for each dressing might also include a small printed image or diagram of the predicted wound appearance at the time that dressing is intended to be applied, serving as a visual guide for caregivers to compare with the actual wound and confirm that the healing is on track with the model's expectations. The kit as a whole provides a scheduled sequence of dressings, allowing clinicians or patients to simply follow the sequence over the prescribed period. Importantly, because all dressings are custom-fabricated together, the materials and compounds used can be varied stage-by-stage, For instance, the early-stage dressings in the set can be fabricated with a hydrogel base and higher concentrations of antimicrobial agents to manage bioburden and maintain a moist environment, while later-stage dressings might be fabricated with a gauze or semi-permeable matrix to allow the wound to breathe as it finishes healing, possibly incorporating analgesics or collagen to support tissue remodeling instead of antimicrobials. The packaging ensures sterility and clearly organizes these dressings in the correct order, effectively turning the individual custom dressing concept into a comprehensive wound treatment package that evolves with the patient.

Machine Learning for Wound Progression Prediction

Underlying the predictive capability of the system is a machine learning component trained specifically on temporal wound data. The invention preferably employs a multistage predictive wound model implemented as a machine-learning algorithm that has been exposed to large datasets of wounds tracked over time. These datasets may include sequences of multispectral images and 3D models (voxel-based representations or surface meshes) of various wound types healing under known conditions, thereby teaching the model typical patterns of progression.

For example, a training dataset might consist of weekly scans of diabetic foot ulcers from presentation to full closure, or serial images of surgical wounds from post-operation through scar maturation. By learning from many such sequences, the model develops the ability to forecast future wound states from a given initial state. In one implementation, the predictive model is a temporal convolutional neural network (CNN) that ingests the current wound's image and geometric data and produces a prediction of what the wound will look like at the next time step. A temporal CNN can slide over sequences of past wound states (if available) to detect healing trends, or it can use one-time input augmented with known healing rates. In another embodiment, a transformer-based machine learning model is utilized; this model can take as input a series of encoded wound representations (such as a sequence of wound volume grids or feature vectors derived from images over time) and then generate future wound representations by attending to patterns learned from the training data.

The mention of "voxelated wound volumes" refers to a method of representing a wound in 3D as a set of volume elements (voxels) containing tissue state information, such representations, captured at successive time points, can be fed into a 3D convolutional network or a transformer that handles spatial data, enabling the model to predict how each portion of the wound volume might change (for instance, which voxels will fill in with new tissue by the next stage). The predictive model may incorporate both spatial features (the layout of tissue types in the wound) and temporal dynamics (the rate at which those tissue types typically change) in making its forecasts. During operation, the system's processing unit uses the trained model by providing it the current wound classification map and surface model (and possibly previous states if the wound has been imaged before) and running an inference to obtain predicted classification maps and surface models for future time points.

Specific machine learning architectures can include convolutional LSTM (Long Short-Term Memory) networks (combining convolution for spatial detail with recurrent-like steps for temporal sequencing), or encoder-decoder networks where the encoder processes the current wound state and a decoder generates the future state conditioned on learned wound-healing trajectories. The model might output not only a single future state but a series of them (e.g., a prediction for week 1, week 2, week 3, etc.), effectively simulating the wound's healing as a sequence. These predicted outputs are then converted into the design specifications for the sequential dressings as described. The system can be configured to continuously improve its predictive accuracy by incorporating feedback; for instance, if the patient returns for a follow-up and a new scan of the wound is taken, the system can compare the actual wound state to the previously predicted state for that time, and use the difference to adjust the model (either by retraining or by parameter tuning), thereby refining subsequent predictions and any not-yet-fabricated dressings.

Adaptive Dressing Design at Each Healing Stage

Because the wound characteristics are expected to evolve, each dressing in the time-sequenced set is adaptively designed to meet the anticipated needs of its corresponding healing stage. At the core, the digital fabrication file for each stage encodes a custom geometry that matches the predicted wound surface at that stage. For example, if the wound is predicted to become shallower and smaller in diameter over two weeks, the second-week dressing will have a correspondingly reduced concave depression to match the new wound depth and a smaller footprint to conform to the contracting edges.

The thickness of dressing material in different regions can also be varied per stage: an early-stage dressing might be thicker in areas expected to experience high exudate levels (to provide absorption), whereas a later-stage dressing can be thinner overall since the wound is drier and nearly closed. In addition to geometry, the material composition of each dressing is selected based on the predicted tissue composition underneath. Early in healing (or in wounds healing by secondary intention with open areas), a hydrogel-based dressing material is often beneficial to maintain moisture and facilitate autolytic debridement; thus, the first one or two dressings in the sequence might be predominantly a hydrogel polymer matrix.

As the wound bed becomes cleaner, fills with granulation tissue, and begins to epithelialize, excessive moisture may not be needed and instead protecting new tissue and preventing adherence is key, later stage dressings might transition to semi-permeable films or gauze-like materials, which are more breathable and less hydrating, to avoid maceration of the new skin. This invention allows such a material transition to be built into the series: for instance, Dressing 1 could be a conforming hydrogel pad with embedded antimicrobial silver particles over an area of necrotic tissue, whereas Dressing 3 (a later-stage dressing) could be a mesh scaffold or collagen-infused gauze to support tissue remodeling once the wound is largely clean. Similarly, the therapeutic compounds embedded in the dressings are adjusted stage by stage.

The system's initial wound classification might indicate, for example, a high bioburden (bacterial load) and necrotic tissue, so the first dressing is fabricated with potent antimicrobial agents (such as silver, iodine, or an antibiotic)

concentrated in regions overlying the infected or necrotic areas, as well as proteolytic enzymes in hydrogel form to aid debridement. After a round of treatment, the wound's predicted future state may have reduced infection and begun forming healthy tissue; thus the next dressing can shift focus by including growth factors or collagen in the wound-contact layer to stimulate granulation and analgesic compounds to manage pain if the granulating tissue is sensitive.

By the final stages, if the model predicts an almost healed wound or a fresh scar, the dressing might contain silicone gel or vitamin E in the pad to minimize scar formation and keep the new tissue supple. The ability to pre-plan these transitions means each dressing is specialized: there is no one-size-fits-all throughout the healing process, but rather a deliberate, stage-specific formulation. The digital fabrication files carry these instructions—e.g., at stage 2, incorporate a slow-release angiogenic factor in the central region to encourage blood vessel growth in new tissue, or at stage 3, reduce the concentration of antimicrobials since the wound bed is now mostly healthy tissue.

During fabrication, the multi-material 3D printer executes these specifications by switching printhead cartridges or mixing bio-inks, so that each dressing emerges with the intended spatial distribution of materials and drugs that align with the wound's stage. The result is a time-coordinated series of dressings where each one is optimized for a particular snapshot of the wound's healing journey. This level of adaptation at each stage improves clinical outcomes by always providing the wound with the right environment, cleansing and bactericidal in early days, moist and regenerative in mid-healing, and protective in the final phase. Furthermore, because the dressings are made in advance (based on predictions), the patient or caregiver can be instructed to apply them in sequence without the need for rescanning at every change, unless a significant deviation in healing is observed.

If the wound's actual healing deviates from the model (for example, healing slower than predicted), the system can be used to take a new interim scan, update the healing model and adjust the remaining dressings or generate additional ones as needed, providing a flexible yet structured approach to long-term wound management.

Clinical Examples of Sequential Healing
Application

This predictive, time-sequenced dressing system can be illustrated by several real-world clinical scenarios. In one example, consider a diabetic foot ulcer (a chronic wound) being managed by secondary intention healing. At the initial visit, the wound is large, with a mix of necrotic tissue and some infected areas; the system's imaging captures this and the first dressing is printed as a thick hydrogel pad infused with antimicrobial and debriding agents to address infection and slough. The predictive model, trained on many diabetic ulcer cases, projects that after two weeks of proper care the ulcer will be smaller in radius, have a clean granulating base, and significantly less exudate. Accordingly, the system produces a second dressing design for that two-week mark: this dressing is smaller, with a scaffold structure to support new tissue in the cavity and containing growth factors to accelerate granulation. A third predicted stage might be near closure—the model anticipates just a shallow pink epithelializing area, so the system fabricates a final dressing, a thin silicone-backed film just to keep the new tissue protected.

These dressings are packaged and labeled week 0, week 2, week 4. As the patient uses them, the wound indeed progresses; by week 2, they apply the second dressing which fits snugly on the reduced wound and delivers the next set of therapeutics. By week 4, the wound resembles the prediction closely, so the third dressing is appropriate and helps finalize the healing. If, hypothetically, the wound was healing slower than expected, the patient or clinician could take a new scan at week 2; the system's model would update, and a revised third dressing (or even a fourth) could be generated to adapt to the new timeline. This showcases improved care for chronic wounds by planning ahead yet staying responsive.

In another scenario, a surgical incision heals by primary intention. A surgeon closes a long incision (for example, after a joint replacement surgery) with sutures. The wound is expected to heal quickly, but the system can enhance postoperative care by imaging the closed incision and predicting the normal course of healing (typically rapid epithelial closure in a matter of days). The system fabricates two dressings: the first is a conformal dressing with antimicrobial properties and cushioning to be placed immediately over the closed incision (protecting it and preventing infection during the critical first few days).

The model predicts that by a week later, the incision will have mostly sealed and entered a maturation phase; thus a second dressing is designed primarily as a light protective cover with silicone gel to reduce scar formation. The kit is provided to the patient upon discharge: "Dressing 1-apply now, remove after 3 days; Dressing 2-apply on day 4 and wear for the next week." Each dressing is custom-fit to the incision line and surrounding anatomy of that patient (say, around a knee or hip), unlike generic postoperative bandages. By having the second dressing ready, the patient can self-apply it at home at the appropriate time without needing an interim clinic visit, unless an issue arises. The predictive model in this case is straightforward because primary intention healing is usually linear and fast, but it still ensures that the later dressing is optimized for the incisional scar management rather than the immediate post-surgery needs.

As a third example, a patient with a severe burn wound requires periodic debridement and will eventually be grafted—a situation involving tertiary intention healing (delayed closure). Initially, the burn wound is imaged after the first debridement: it's an open wound with mixed depth areas. The system's model forecasts two phases: an intermediate phase where the wound is being kept open and prepared for graft (with frequent debridement, needing infection control and moisture balance), and a later phase post-grafting where the wound (now grafted with skin) needs support to integrate the graft and heal the edges. In response, the system fabricates a sequence of dressings for these phases. The first few dressings (labeled 1A, 1B for use over a couple of weeks) are full-size custom dressings covering the burn area, loaded with antimicrobials and moisturizing hydrogel to manage the wound bed while open. Then, once the surgeon applies a skin graft (e.g., at week 3), the model has anticipated a second stage: the system provides a dressing design specifically for post-graft protection, a dressing that conforms over the grafted area, possibly with silicone and VASELINE® gauze components to keep the new graft moist and protected, and with less pressure on areas likely to blister. This dressing (labeled Stage 2) is applied immediately after grafting. Additionally, a third dressing (Stage 3) might be prepared for a final healing stage, where the graft is stable and just needs light covering and scar modulation. By planning these ahead, the care team has a tailored dressing ready at each critical juncture: initial wound stabilization, post-graft coverage, and final scar management. This reduces delays in treatment and ensures optimal conditions at every step, leveraging both prediction and real-time adaptation (since the decision to graft is fed into the model as a trigger for switching to the next set of dressings).

Across these examples, the benefit of modeling and pre-fabricating sequential dressings is clear. The patient receives a continuum of care in the form of a personalized dressing regimen. The clinician can still monitor the wound at each dressing change and has the flexibility to adjust if reality diverges from predictions, but in many cases the wound will follow a known trajectory that the model accurately captures. The invention thus marries predictive analytics with digital fabrication in wound care: it not only assesses and treats the wound's present state, but also looks ahead and actively prepares for the wound's future states, providing a library of custom therapeutic tools (the dressings) that are ready for use at the appropriate times. This reduces the need for one-off dressing fabrication at each visit, shortens response time to changes in the wound, and standardizes care by ensuring each stage of healing is managed with a purpose-built solution.

Figure 9:
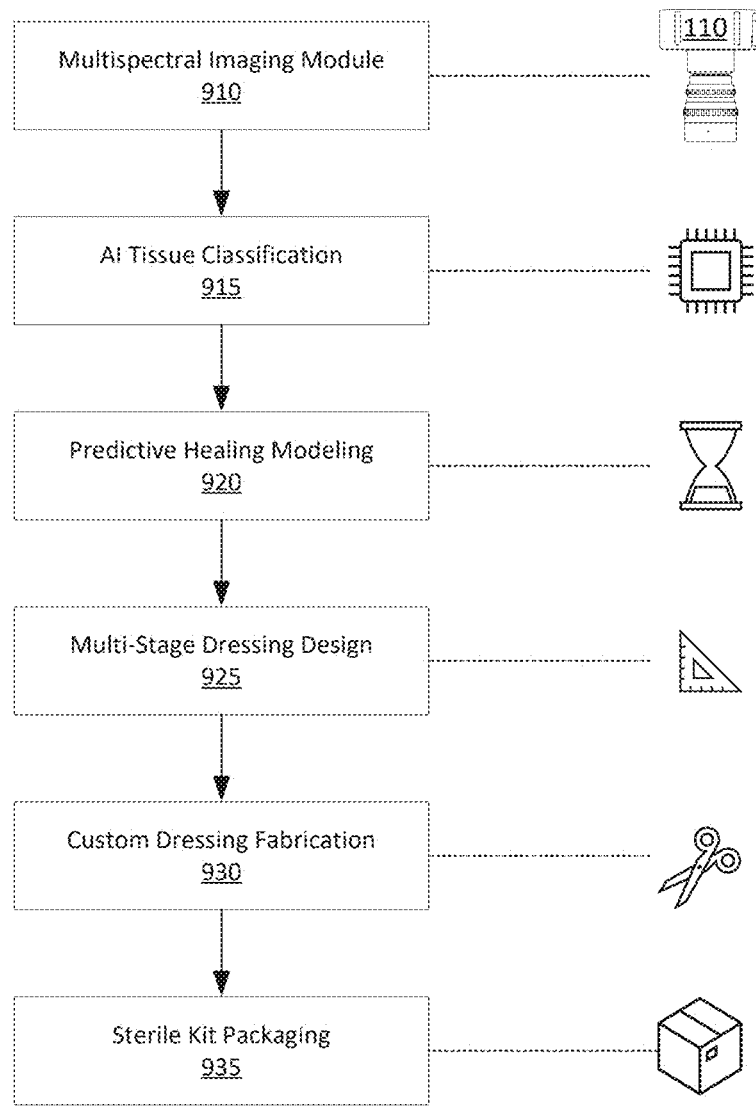
FIG. 9 is a flowchart illustrating a predictive modeling and time-staged dressing fabrication process according to an embodiment of the invention, in which wound data is analyzed to forecast healing stages and multiple custom dressings are designed and fabricated in advance.

Referring now to FIG. 9, a process workflow diagram is illustrated, comprising steps 910 through 935, each corresponding to a functional element of the inventive method (and aligning with claim steps such as image capture, analysis, design, and fabrication). At step 910, an image of the patient's wound is acquired using the system's imaging apparatus. This may include capturing multi-spectral photographs and depth data (e.g., 3D scans), providing the raw wound data for analysis (step 910 corresponds to the image acquisition element of the claims). Next, at step 915, the system performs machine-learning modeling on the captured data—for example, generating a wound tissue classification map and quantifying wound dimensions. In this step, a trained AI algorithm analyzes the spectral images to distinguish tissue types (granulation, slough, necrosis, etc.) and constructs a three-dimensional wound model with labeled regions. This 915 step implements the ML-based wound assessment claim element, producing a detailed digital model of the wound's current state.

At step 920, the process uses the analyzed wound model to automatically design a customized therapeutic dressing. This includes computationally defining the dressing's 3D geometry to conform to the wound topology, selecting or optimizing the materials for each region (e.g., hydrogel versus foam), and determining the distribution and dosage of any embedded therapeutic agents tailored to the tissue needs identified. The design step 920 thus corresponds to the claim element of generating a patient-specific dressing specification. In the next step 925, the system translates the design into manufacturing instructions and an application regimen, for instance, generating the multi-layer print pattern or bill of materials for fabrication, and formulating a schedule for dressing changes (if part of the treatment plan).

Step 930 then entails fabrication of the custom dressing according to the design. In one embodiment, this is accomplished via a multi-material 3D printer or other automated fabrication apparatus which produces the dressing with the prescribed geometry, layers, and infused compounds (step 930 corresponds to the claimed fabrication or production element). Finally, at step 935, the finished customized dressing is output for clinical use, for example, packaged or handed off for application to the patient's wound. In a method of treatment, step 935 can include actually applying the custom dressing to the wound site in the patient, thus delivering the tailored therapy. Each of these steps (910-935) aligns with elements of the claimed invention, collectively providing an end-to-end solution from wound imaging through to fabricated personalized dressing ready for use.

Figure 10:
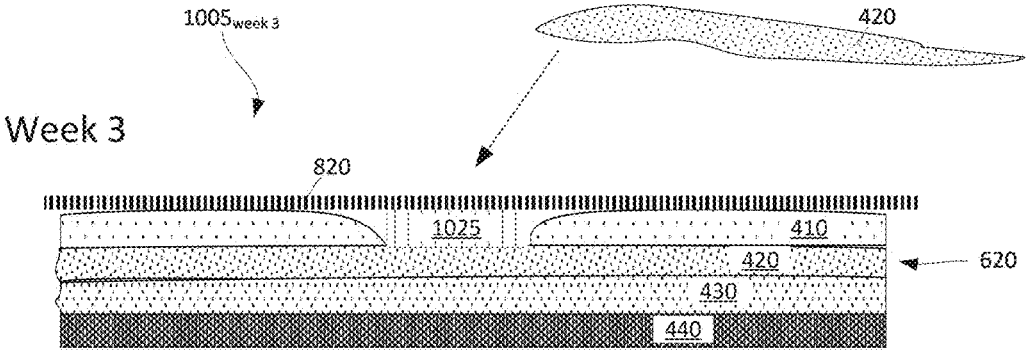
FIG. 10 is a schematic diagram showing multiple wound states over time and matching fabricated dressings for each stage, conceptually depicting an initial wound profile and how the wound size and tissue composition change (e.g., from an open wound to a smaller granulating wound to a nearly closed wound) with a corresponding series of custom dressings aligned below each stage.

This workflow can be repeated in a feedback loop as the wound heals. After the initial dressing is applied, the system may perform new imaging and analysis at subsequent intervals (e.g., weekly) to update the design. FIG. 10 illustrates the clinical and structural progression of a healing wound over three stages: Week 1, Week 2, and Week 3. The corresponding custom dressing designs at each stage are shown (labeled here as $1005_{week1}$, $1005_{week2}$, and $1005_{week3}$ in the illustration). FIG. 10 provides cross-sectional views of the wound and dressing at each stage, demonstrating how the wound's anatomy evolves and how the dressing is adaptively re-designed to match.

In the Week 1 cross-section, the wound is at its initial size and depth (e.g., a considerable defect with regions of necrotic tissue and high exudate). The first-stage dressing $1005_{week1}$ is shown positioned over the wound, comprising at least two layers: a base wound contact layer 1010 and an overlying absorbent layer 1015. In this early stage, layer 1010 may be, for example, a conformal hydrogel loaded with an antimicrobial agent to reduce bioburden in the wound bed. This layer fills the wound cavity and maintains a moist environment while delivering the antimicrobial (as reflected in the Stage 1 JSON example below, layer 1010 contains an antimicrobial at 20 mg/cm$^2$). The second layer 1015 in Week 1 is an absorbent material (such as a foam or alginate pad) that overlies the hydrogel. Layer 1015 manages the heavy exudate typical of an initial inflammatory stage, protecting the surrounding skin from moisture and securing the contact layer in place.

Stage 1—Week 1 ($1005_{week1}$) JSON Example: An exemplary data representation for the Stage 1 dressing design in JSON format is as follows:

```
{
    "dressingId": "1005_week1",
    "stage": "Week 1",
    "geometry": {
        "type": "3DMesh",
        "file": "wound_week1_model.stl",
        "area": "25 cm^2",
        "maxDepth": "5 mm"
    },
    "layers": [
        {
            "layerId": "1010",
            "material": "Hydrogel",
            "thickness": "5 mm",
            "role": "wound contact",
            "therapeutic": {
                "class": "Antimicrobial",
                "concentration": "20 mg/cm^2"
            }
        },
        {
            "layerId": "1015",
            "material": "Absorbent foam",
            "thickness": "3 mm",
            "role": "outer cover"
            // no therapeutic agent in this layer for Stage 1
        }
    ],
    "applicationSchedule": "Week 1: q12h"[001]
}
```

By Week 2, as depicted by the cross-section for $1005_{week2}$ in FIG. 10, the wound has begun to fill in with granulation tissue (the cross-sectional wound profile is shallower and the overall wound area has reduced). The dressing design is correspondingly adjusted. In this intermediate stage, the base layer 1010 can remain in use as a wound contact layer but with a modified formulation: for instance, the hydrogel could be mixed with collagen or a bioresorbable scaffold material to support tissue in-growth, and the concentration of antimicrobial in layer 1010 may be reduced (e.g., from 20 mg/cm$^2$ to 10 mg/cm$^2$) as infection is brought under control. Additionally, a therapeutic agent promoting regeneration may be introduced at this stage—for example, layer 1010 in the Week 2 dressing might carry a growth factor (as shown in the Stage 2 JSON, layer 1010 includes a GrowthFactor at 5 mg/cm$^2$ alongside a lower dose antimicrobial).

Stage 2—Week 2 ($1005_{week2}$) JSON Example: Similarly, an example JSON structure for the Stage 2 dressing design is:

```
{
    "dressingId": "1005_week2",
    "stage": "Week 2",
    "geometry": {
        "type": "3DMesh",
        "file": "wound_week2_model.stl",
        "area": "18 cm^2",
        "maxDepth": "3 mm"
    },
    "layers": [
        {
            "layerId": "1010",
            "material": "Hydrogel",
            "thickness": "4 mm",
            "role": "wound contact",
            "therapeuticAgents": [
                {
                    "class": "Antimicrobial",
                    "concentration": "10 mg/cm^2"
                },
                {
                    "class": "GrowthFactor",
                    "concentration": "5 mg/cm^2"
                }
            ]
        },
        {
            "layerId": "1015",
            "material": "Absorbent foam",
            "thickness": "2 mm",
            "role": "outer cover"
        }
    ],
    "applicationSchedule": "Week 2: q8h"
}
```

The overlying layer 1015 in Week 2 remains an absorbent or moisture-managing layer to handle moderate wound exudate, continuing the role it served in Week 1. The physical dimensions of the dressing are updated to match the wound's new size: FIG. 10 shows that the span of layers 1010 and 1015 in $1005_{week2}$ is smaller than in Week 1, and the thickness of the layers may also be reduced in accordance with the shallower wound depth. Thus, the dressing in Week 2 provides a balance of continued antimicrobial protection and enhanced regenerative support, tailored to the wound's transitional state.

By Week 3, the wound has substantially healed in the cross-sectional view (FIG. 10, $1005_{week3}$). The wound bed is largely filled with new tissue and epithelialization is underway, leaving only a shallow depression or fragile new skin (the illustrated wound profile is much shallower, with only a thin layer of healing tissue exposed). The custom dressing design for this final stage reflects a shift in therapeutic focus and material composition. The base layer 1010 in the Week 3 dressing can be further refined into a delicate bioactive scaffold or a collagen-infused hydrogel film that covers the remaining wound area. In this stage, layer 1010's primary role is to keep the wound moist and deliver growth factors or other epithelium-promoting compounds to accelerate final closure; it no longer needs high levels of antimicrobial, since the infection risk is minimal by this point (indeed, in the Stage 3 JSON example, layer 1010 contains only a growth factor at 10 mg/cm² and no antibacterial agent).

Stage 3—Week 3 (1005$_{week3}$) JSON Example: Finally, an example JSON for the Stage 3 dressing design is:

```
{
    "dressingId": "1005_week3",
    "stage": "Week 3",
    "geometry": {
        "type": "3DMesh",
        "file": "wound_week3_model.stl",
        "area": "15 cm^2",
        "maxDepth": "1 mm"
    },
    "layers": [
        {
            "layerId": "1010",
            "material": "Collagen-infused hydrogel",
            "thickness": "2 mm",
            "role": "wound contact",
            "therapeutic": {
            "class": "GrowthFactor",
            "concentration": "10 mg/cm^2"
            }
        },
        {
            "layerId": "1025",
            "material": "Silicone film",
            "thickness": "0.5 mm",
            "role": "protective cover"
        }
    ],
    "applicationSchedule": "Week 3: q6h"
}
```

The absorbent layer 1015 used in earlier weeks is no longer needed for heavy fluid management and is replaced by layer 1025 in the Week 3 design. Layer 1025 is a different material optimized for the final healing stage, for example, a thin silicone film or semi-permeable membrane that protects the new epithelial tissue and prevents external contamination while minimizing adherence to the fragile skin. This layer 1025 (illustrated in FIG. 10 as the new top layer in 1005$_{week3}$) is flexible and atraumatic, serving to maintain a moist wound environment and shield the area without the bulk of a foam. The use of a silicone or film layer also helps reduce scarring (silicone dressings are known to modulate scar formation), aligning with the therapeutic goals of the late stage. Accordingly, FIG. 10 shows material evolution from layer 1015 to 1025, the absorbent layer present in Weeks 1-2 is substituted by a protective interface layer in Week 3, marking a clear change in dressing structure and composition as healing progresses.

In addition to topology and material changes, the system dynamically modifies the application frequency of the dressings across healing stages. The time-windowed schedules encoded in the JSON examples reflect this adaptive frequency logic. For instance, in one implementation the initial stage dressing (Week 1) is changed at a moderate interval of about every 12 hours (notated "q12 h"), amounting to roughly 14 dressings per week in the first week. By contrast, in the Week 3 stage the system may increase the change frequency to every 6 hours ("q6 h"), which corresponds to approximately 28 dressings in a week. FIG. 10's depicted timeline and the associated data indicate this change—for example, a note in the plan might specify "Week 1: q12h;

Week 3: q6h," meaning that in later stages the dressing is swapped more frequently. The rationale for this in one scenario is that as the wound becomes smaller and enters the regenerative phase, more frequent dressing changes can provide a sustained delivery of growth factors or other therapeutics at high intervals without concern of maceration (since exudate levels are low by Week 3).

The increased frequency ensures the wound bed is consistently supplied with fresh bioactive stimulus (and that the delicate new tissue is regularly inspected). In another scenario or wound type, the system could apply the opposite logic, tapering down the dressing change frequency as the wound stabilizes, for example, an aggressive early schedule (e.g., q6 h in Week 1-2 for intensive infection control) might later reduce to q12 h in Week 3 as the wound closes. The scheduling engine can thus flexibly adjust the regimen based on real-time healing status, which is one of the advantages of the invention's data-driven approach. These time schedules are communicated in concise clinical notation (q6h, q12h, etc.) and can be directly integrated into treatment orders in the patient's record. By encoding the dressing design and its application schedule in a machine-readable format (such as the JSON structures above), the system ensures that manufacturing systems and EHR systems stay synchronized with the patient's personalized wound care plan.

Overall, the progression depicted in FIG. 10 underscores the rationale for dynamic modification of the dressing design over time. As the wound's anatomy changes (healing from a deep, broad defect in Week 1 to a shallow, epithelializing surface by Week 3), the topology of the dressing is re-customized to maintain an exact fit—this ensures optimal contact at the wound interface and coverage of the wound area at each stage. Simultaneously, the layer materials and impregnated therapeutic compounds are deliberately altered to suit the evolving therapeutic needs: early on, priority is given to debridement and infection control (hence a drug-loaded hydrogel and absorptive foam); mid-course, the focus shifts to granulation support (a scaffolded hydrogel with growth factors); and in the final stage, the emphasis is on gentle protection and tissue remodeling (a silicone film protecting new skin, with agents to promote epithelial maturity or reduce scarring).

FIG. 10's three-stage sequence visually correlates these changes in the dressing to the underlying changes in the wound tissue beneath, for example, the replacement of layer 1015 with layer 1025 between Week 2 and Week 3 aligns with the wound no longer producing significant exudate and needing a different care strategy. By dynamically adapting both the physical design and the biochemical components of the dressing in tandem with the patient's healing trajectory, the system provides a more responsive and effective treatment than a static, one-size-fits-all dressing. This iterative, data-informed approach (illustrated by the workflow of FIG. 9 and the stage-wise depictions of FIG. 10) ensures that at each phase of healing, the patient receives a custom-fabricated dressing optimally configured for their current condition, thereby potentially accelerating healing and improving outcomes.

Wound Dressing Fabrication

Subtractive Layer-Based Fabrication System

In one embodiment, the wound dressing fabrication apparatus employs a subtractive, layer-by-layer construction approach. Pre-manufactured sheet materials (for example, hydrogel film sheets, medical gauze, or polymeric barrier films) are selected and cut to match the exact geometry of each layer in the designed dressing. The digital 3D dressing model is virtually "sliced" into discrete layers, and for each layer the apparatus cuts a sheet along its perimeter to the specified shape.

A computer-controlled cutting module, such as a CNC blade cutter or a laser cutter-traces the outline of the layer on the material sheet, following the contours defined by the dressing's design file. Each sheet corresponds to a different stratum of the final dressing, so that when the layers are later stacked in order, they recreate a dressing that conforms exactly to the wound topology in all dimensions. This subtractive system integrates mechanisms for handling multiple types of sheet materials. It can load or store an array of substrate sheets, including those pre-impregnated with therapeutic compounds and those without. For instance, one cartridge may supply an alginate hydrogel sheet imbued with antimicrobial agents, while another provides a plain absorptive foam or gauze layer.

The apparatus's control unit selects the appropriate sheet type for each layer based on the digital dressing specification (e.g., selecting a drug-loaded hydrogel sheet for a layer that will contact an infected tissue region, versus a simple protective film for an outer layer). A modular sheet feeding mechanism, such as a multi-tray library or roll-to-sheet feeder, allows different substrates to be queued and fed into the cutting area as needed, providing flexibility in material composition for each dressing layer. This modularity in substrate loading ensures that a wide range of dressing designs, varying in materials and embedded compounds, can be fabricated without retooling the machine.

After cutting, the system places each layer in the correct stacked position to build the composite dressing. Precision alignment of layers is important: the apparatus may use alignment pins, registration holes, or optical fiducials to ensure each cut piece is positioned with appropriate tolerances on the assembly platform. For example, the platform can include retractable pins that match reference notches on each layer, or a vision system can detect the layer's edges and adjust placement. The alignment tolerance between layers is on the order of a few tens to hundreds of micrometers, so that there is virtually no overhang or mismatch in the final stacked profile.

Maintaining layer-to-layer registration is essential, lateral deviation or rotation of a layer could degrade the final dressing's conformity to the intended shape. The system's software accounts for layer thickness and material properties to ensure that as each layer is added, it fits the "puzzle" of the multilayer stack without distortion. Once each new layer is correctly positioned, the apparatus bonds it to the underlying stack. Bonding can be achieved by applying biocompatible adhesive or by thermal welding, depending on the material combination. In some implementations, the machine includes an adhesive dispensing unit that applies a thin film of medical-grade adhesive between layers. Suitable biocompatible adhesives include polyethylene glycol (PEG)-based hydrogel adhesives and fibrin glue sealants. For example, a PEG hydrogel adhesive (such as the DURASEAL™ surgical sealant) can be micro-dispensed along the perimeter or across the surface of a layer before the next layer is placed, forming a strong yet absorbable bond when cured.

Likewise, a fibrin sealant (e.g., TISSEEL™) can be applied; when the subsequent layer is laid down, the thrombin and fibrinogen components mix and polymerize into a fibrin clot that glues the layers together. These adhesives are advantageous because they form bonds and then safely biodegrade over time.

In alternative cases where the layers are made of thermoplastic or thermoset films, the apparatus may use thermal bonding: for instance, a heated platen or ultrasonic welding head can briefly press the new layer onto the stack, melting a thin interface that solidifies upon cooling to fuse the layers. The system's control can regulate the temperature and pressure of this bonding step to avoid damaging any heat-sensitive therapeutic compounds embedded in the layers.

The mechanical architecture of the subtractive fabrication system ensures both precision and repeatability in layer fabrication. The cutting head and assembly platform are typically driven by a multi-axis motion control system. For example, an X-Y gantry may be driven by toothed belt drives for high-speed lateral motion, while the Z-axis (used for raising/lowering the assembly platform or moving the cutting/placement head vertically) is driven by a lead screw actuator for fine positional control. Belt drives allow rapid movement across the cutting plane to expedite shaping of each layer, whereas lead screw drives provide high accuracy and minimal backlash, which is ideal for precise vertical placement of layers.

The combination of belt and lead screw actuators harnesses the strengths of each: belts deliver speed and range, and lead screws deliver accuracy and repeatable positioning. Stepper motors or servo motors with encoder feedback typically power these actuators. The control software translates the digital dressing file into motion commands (e.g., G-code or a similar instruction set) that drive the X-Y-Z stages to cut the exact 2D profile for each layer and then to align and place the layer in the stack. By calibrating the stepper motor steps or servo encoder counts to real-world units, the system can achieve sub-millimeter or even sub-100 micron precision in cutting and placement. Additionally, if needed for quality control, the apparatus can include sensors (such as laser displacement sensors or cameras) to verify the dimensions of each cut layer and its placement accuracy before proceeding to the next layer, adjusting as necessary to stay within alignment tolerances.

After the final layer is placed and bonded, the apparatus produces a fully assembled multi-layer dressing that mirrors the wound's topography and contains any specified therapeutic zones (as designed in the digital model). At this stage, dressing retrieval and sterile handling become important. The embodiment includes features to handle the finished dressing in a manner that maintains sterility. For example, the assembly platform may double as a sterile transfer tray: once fabrication is complete, a robotic manipulator or pick-and-place arm lifts the completed dressing (or the platform holding it) and moves it into a sealed output compartment.

This entire process can occur within a controlled sterile enclosure, the fabrication chamber can be equipped with HEPA-filtered air flow or UV light sterilization so that the environment remains aseptic during assembly. The materials themselves (sheets and adhesives) are preferably pre-sterilized before loading. The result is that the custom dressing can be packaged or delivered without further contamination.

In some designs, the apparatus may even directly package the dressing (e.g., placing it into a sterile pouch and sealing it) as the final step. The modular design of the subtractive system, including interchangeable cutting tools (blade, laser, etc.) and adjustable feeders for various substrates, makes it versatile for different dressing configurations while consistently achieving high precision in layer fabrication and assembly.

Additive Printing Fabrication System

In another embodiment, the fabrication apparatus is an additive manufacturing system that directly builds the wound dressing in three dimensions by depositing materials layer by layer. Instead of cutting preformed sheets, this system uses one or more print heads to extrude or jet therapeutic fluids, hydrogels, pastes, or gels in precise patterns, effectively "printing" the dressing according to the wound-conforming digital design. The dressing is constructed on a print substrate or build platform, and the geometry is achieved by controlled deposition of material at coordinates corresponding to the wound topology and dressing structure.

This additive system comprises a multi-axis motion platform (X-Y-Z) and multiple material dispensing heads, all governed by a centralized control unit. The motion control hardware is comparable to that of a high-end 3D printer or robotic deposition system: the print head carriage moves in the horizontal plane (X and Y axes) over the build area, and either the head or the build platform moves vertically (Z axis) to increment the layer height. High-speed belts can be used on the X-Y axes for rapid movement between deposition points, while a lead screw or ball screw mechanism precisely drives the Z axis to set exact layer heights and to maintain fine control during printing.

Each axis is actuated by stepper motors or servo motors, enabling controlled motions with resolutions often in the tens of micrometers. The software interpretation of the 3D dressing file involves slicing the model into thin horizontal layers (the layer thickness can range from tens to a few hundred micrometers, depending on required resolution). For each layer, toolpaths are generated for each print head, dictating where and how much material to deposit. These toolpaths can be continuous curves following the dressing contours or a raster of point-by-point deposition, or a combination, depending on the material and the desired microstructure.

A feature of this embodiment is its multiple printhead system for multi-material capability. The apparatus can incorporate, for example, several syringe-based extruder heads or inkjet nozzles, each loaded with a different composition. One printhead might extrude a hydrogel (such as a collagen or alginate gel) that is loaded with cells or growth factors for bioactive wound healing; another might dispense a paste containing antimicrobial silver particles or antibiotics; yet another could deposit a more viscous silicone or polyurethane polymer to form a supportive or adhesive frame of the dressing. The printheads are mounted such that they can either operate sequentially within the same layer or concurrently in different regions, without interfering with each other. The control system carefully coordinates these heads to deposit the right material in the right place as defined by the heterogeneous dressing design. This allows the fabricated dressing to have distinct therapeutic regions, for example, a section of the dressing that will contact necrotic tissue can be printed with a hydrogel containing enzymatic debridement agents, while another section for a high-exudate area can include a printed absorbent foam-like polymer with moisture management properties.

The multi-head arrangement can either have fixed heads each fed by its material reservoir or a quick-change tool head that swaps materials on the fly; in both cases, alignment of the different materials within a layer is assured by the shared coordinate system. Nozzle and material control in the additive system are sophisticated to ensure each material is deposited under optimal conditions. Each printhead may include temperature control (heating or cooling) and pressure/flow control. For instance, if a certain bio-ink gel is too viscous at room temperature, the nozzle can be maintained at a slightly elevated temperature (e.g., 37-40° C.) to reduce viscosity for smooth extrusion.

Conversely, materials that cure upon cooling could be chilled as they extrude. The apparatus can also incorporate UV or visible light sources if using photo-curable biomaterials (some hydrogel precursors or adhesive formulations solidify when exposed to light). In such cases, a UV lamp might be mounted adjacent to the print nozzle to immediately cure the deposited filament in situ. Additionally, environmental control of the build chamber, regulating ambient temperature, humidity, and sterility, helps maintain material performance. For example, hydrogel printing often benefits from a humid environment to prevent premature drying of the gel; the system can enclose the build area and keep humidity high.

All these thermal and environmental controls ensure that each deposited layer maintains its intended shape and that the integrity of sensitive bioactive compounds is preserved during fabrication. Key to the additive approach is volumetric dosing accuracy for the deposited materials. The system's extrusion controllers are calibrated to dispense specific volumes; for syringe or piston extruders, this could mean using stepper motors with known linear step-to-volume mappings (e.g., a certain number of microsteps per microliter of material extruded). For inkjet-style print heads or micro-valve dispensers, the volume of each droplet is tightly controlled by the nozzle design and firing parameters, often on the order of picoliters to nanoliters per drop.

Modern inkjet bioprinters can eject on the order of 10,000 droplets per second from each nozzle, enabling very fast area filling with tiny deposits. The apparatus leverages this to create either continuous features or finely voxelized deposition patterns. In regions where a uniform fill is needed, the printer can trace continuous paths (e.g., a continuous bead of hydrogel following a zig-zag infill across the layer). In regions where a gradient or more discrete pattern is needed, it can deposit material as an array of small droplets, building up a micro-structured layer.

For example, a gradient in drug concentration could be achieved by varying the density of droplets containing a drug across that layer. The motion control is versatile enough to handle both modes: it can move in a smooth continuous motion for extrusion or pause and move in a point-to-point fashion synchronized with droplet release for inkjet deposition. By combining these strategies, the additive system achieves both high structural fidelity and precise placement of therapeutics at the microscale.

To ensure each new layer of printed material aligns correctly with the previous layers (which is important since material can sometimes slightly spread or shrink), the apparatus may employ a layer registration check. This could involve a built-in camera or sensor that scans the topography of the partially printed dressing before adding the next layer. The control software can then adjust the upcoming toolpaths if necessary to compensate for any minor deviations, maintaining overall dimensional accuracy. The typical layer alignment tolerance in such a system is on the order of the print resolution (often 50-100 μm laterally). Within that tolerance, the printed multi-layer structure will closely match the CAD model (e.g., referenced in the exemplary JSON above) of the dressing in both shape and the distribution of different materials.

After the final layer is deposited, the additive fabrication system may perform any required post-processing to finalize the dressing. This can include crosslinking a hydrogel (via cooling or chemical crosslinker spray), full curing by light exposure if not done layer-wise, or even a gentle drying step if the design calls for a semi-dry scaffold.

The end result is a cohesive, monolithic dressing that can be lifted off the build plate. Dressing retrieval in this embodiment is often facilitated by the build platform itself: for instance, the dressing might be printed on a disposable sterile liner or a sacrificial layer that can be peeled away, ensuring the underside of the dressing is not contaminated by the platform. A robotic arm or automated spatula tool can then remove the dressing and place it into a sterile package.

The entire printing process can be conducted in a sterile environment (e.g., an enclosed chamber with UV sterilization cycles and filtered air). Moreover, components that contact the deposited material, such as nozzles, syringe barrels, or the build tray, can be modular and designed for one-time use or easy sterilization between runs. By adhering to medical device manufacturing standards (ISO class cleanroom conditions, etc.), the additive system produces dressings ready for clinical use without manual intervention that could introduce contaminants.

Hybrid Layering and Printing System

A third embodiment combines both subtractive and additive techniques in a hybrid fabrication unit to capitalize on the advantages of each. In this system, rigid or semi-rigid layers (like films, foams, or fabric gauze) can be cut and stacked as a structural base, after which softer gels or fluidic components are additively deposited onto or within that preformed structure. The result is a composite dressing that, for example, might have a sturdy scaffold or backing layer produced from pre-cut material and highly customized gel or paste regions printed in situ for therapeutic delivery.

Mechanically, the hybrid apparatus integrates a cutting/ stacking module and a printing module within one coordinated platform. One implementation is a machine that initially operates in a "cut-and-place" mode: a sheet material is unrolled or taken from a tray, cut to shape, and placed onto an assembly pallet. Multiple such layers can be sequentially added, just as in the subtractive embodiment, to build up a base dressing (for instance, two or three layers of foam and film to provide structure and absorbency). This pallet holding the partially completed dressing is fixtured to ensure it can be moved or referenced with high repeatability. Once the base layers are prepared, the apparatus switches to "printing" mode.

In some designs, this may involve physically moving the pallet to a different station (e.g. sliding into an adjacent 3D printing gantry) or it may involve a tool change where the cutting head is parked and an extrusion/inkjet print head is brought into position over the same assembly area. In either case, the key is that the coordinate system remains consistent—the control system knows the exact location and orientation of the assembled base layers, so the additive deposition can be aligned to features of those layers. Using the digital dressing file (which encapsulates both the subtractive and additive fabrication instructions), the hybrid system deposits soft materials onto the pre-cut layers in a highly targeted manner. For example, suppose the dressing design calls for an impregnated gel layer in certain wound-contact regions: the machine might have cut out a piece of absorbent foam earlier; now it will print a hydrating hydrogel infused with an antibiotic into a recess or well within that foam layer. The foam could have been pre-cut with a cavity or channel at that spot specifically to hold the gel. The printer head moves into position and fills the cavity with the gel, dispensing a controlled volume that just slightly overfills to account for any shrinkage on curing.

As another example, consider a hybrid dressing where a top breathable film and a bottom absorbent pad were layered; the system could next print a pattern of silicone-based adhesive in dots or lines on the bottom of the pad to create a gentle adhesive surface for skin attachment, or print a localized drug reservoir gel on the side that will contact the wound (e.g., a pocket of slow-release growth factor hydrogel over a region of regenerating tissue). These additive features are applied precisely where intended, since the printer's motion control and the known geometry of the base ensure registration accuracy typically within 0.1 mm. The hybrid apparatus uses precision actuators and sensors to manage the transition between processes. The assembly pallet often includes fiducial markers or reference features that both the cutting system and printing system recognize. After the subtractive steps, a vision system might quickly scan the assembled layers to verify their alignment and dimensions. If any slight shift occurred, the printer's coordinates can be adjusted (a process akin to aligning a printhead with a pre-printed target in industrial printers).

The motion control for both cutting and printing may share common components; for instance, the X-Y platform that moves a cutting laser could be the same that moves the printhead, thereby inherently keeping alignment. Lead screw drives and precision linear guides ensure that when the machine returns to a given XY location, it is repeatable to within a small tolerance, preventing double images or offsets between where a hole was cut and where a fill is printed. The layer alignment tolerance in the hybrid system encompasses both the stacking accuracy of the base layers and the deposition accuracy of printed materials on those layers, again on the order of tens of microns. Maintaining this precision is facilitated by calibration routines and closed-loop feedback (camera verification) before deposition steps.

Bonding and integration of components in the hybrid dressing occur through multiple mechanisms. The base layers might be bonded by adhesives or heat as described for the subtractive system. When the additive materials are deposited, they often inherently bond with the substrate: for instance, a printed hydrogel will mechanically interlock with a porous foam or gauze layer beneath it, especially if it seeps slightly into the pores before gelling.

In other cases, the printer may deposit an adhesive or primer layer to help a printed material stick to a non-porous substrate. For example, if printing a gel onto a pre-cut film, a very thin coating of a PEG adhesive could be printed first as a "tie layer" to ensure adhesion of the gel to the film. The ability to combine both methods means the hybrid apparatus can, in one continuous workflow, create features like channels or micro-reservoirs in the dressing: a channel could be laser-cut in a foam layer, then later filled with a gel containing, say, analgesic medication, thereby creating a drug delivery micro-channel embedded in the dressing. From a software and control perspective, the hybrid unit treats the fabrication as a coordinated sequence of events. The input is a unified 3D design or a set of design files: one part delineates the shapes of pre-cut layers, and another part delineates the additive deposition volumes and paths. The apparatus's control software might first execute a cutting sequence (generating an intermediate 2D vector file for cutting each layer) and then automatically switch to a printing sequence (generating a raster or toolpath for deposition). The user does not need to handle the product in between, the apparatus orchestrates the hand-off. This operation is useful for maintaining sterility and precision: human intervention between steps is minimized or eliminated.

The modularity of the system extends to its tool heads and material handling modules. For instance, the cutting module (whether a laser, blade, or die cutter) can be a removable unit, and the printing module can contain multiple printhead attachments. If a particular dressing design requires no additive component, the printing stage can be skipped or the module not installed; conversely, if no cutting is needed (in some cases the entire dressing might be printed from scratch), the subtractive module can be inactive. In many designs, however, the hybrid approach is used to gain efficiency, cutting out large simple shapes from sheets is often faster than printing that bulk material, and printing is used for the intricate or localized features that sheets cannot provide.

Finally, as with the other embodiments, the hybrid fabrication unit emphasizes sterile handling and output. Because it can involve more than one process, the system is typically enclosed in a single sterile environment so that the product is never exposed to contamination between steps. The transfer of the dressing from the subtractive stage to the additive stage happens within this closed environment. Upon completion, the hybrid machine can present the finished dressing for retrieval in a sterile manner. For example, the assembly pallet can be designed as a sterile tray that doubles as packaging, once the dressing is done, a lid can be sealed over the tray. Alternatively, a robotic arm inside the chamber might insert the dressing into a sterile pouch and seal it. The apparatus may include features like UV lamps that periodically sterilize the internal surfaces, and all materials introduced (sheets, inks, etc.) are pre-sterilized, maintaining an aseptic chain. The result is a custom-fabricated, multi-layer therapeutic dressing that is ready for immediate use on a patient.

This detailed description should be read as an enabling disclosure of various embodiments and not as limiting. The figures (FIGS. 1 through 8B) illustrate one or more example implementations to aid understanding. Modifications and adaptations can be made, for instance, more than four spectral bands could be used (additional light sources beyond 111a-111d for finer spectral resolution), or the dressing fabrication could involve pre-formed inserts combined by the apparatus rather than printing everything (e.g., the system could cut a collagen sponge to shape for element 850 and then cover it with a printed layer 820). All such variants are intended to be encompassed by the invention, which is defined by the claims but supported by the detailed system and method description provided above.

Glossary of Claim Terms

Classification algorithm means a computational procedure designed to categorize input data into defined classes based on specific features or patterns. In the context of the present wound tissue classification system, this term refers to the programmed method that analyzes the multispectral dataset and other sensor inputs to identify different types of tissue present in a wound. The classification algorithm may incorporate or consist of a machine-learning model trained on examples of wounds with known tissue outcomes, enabling it to recognize spectral and spatial patterns that correspond to particular tissue types or conditions. This algorithm processes the collected multispectral images, thermal imaging data, and any available ultrasound data to determine which regions of the wound correspond to various tissue categories, such as viable granulation tissue, necrotic tissue, or epithelializing tissue at the wound margins. As a result, the classification algorithm produces an output that delineates the wound into distinct wound tissue regions, with each region associated with spatial coordinate-specific tissue conditions. Implemented as software executed by a processor, the classification algorithm operates consistently across different wound sizes and skin tones, ensuring that its tissue classification results are reliable and aligned with the invention's objective of accurate, repeatable wound assessment. In this way, the classification algorithm provides the foundational analysis that guides subsequent customized treatment actions in the system.

Depth sensor means a device or component configured to measure, in a non-contact manner, the distance from the imaging apparatus to surfaces in the field of view, thereby capturing three-dimensional shape information. In this invention, a depth sensor is integrated into the imaging apparatus to record the topography of a wound alongside the multispectral images. The depth sensor can operate by emitting signals (such as light or sound) and detecting their reflections to calculate distances; examples include a time-of-flight camera that measures the round-trip time of light pulses or a structured-light system that projects a known pattern onto the wound surface and infers depth from pattern distortion. Data from the depth sensor are used to generate a three-dimensional digital surface model of the wound, providing accurate spatial geometry including wound depth, area, and volume. By obtaining coordinate-specific depth information, the system can correlate each wound tissue region with its corresponding physical location and elevation on the wound bed. The depth sensor's output ensures that the subsequent custom wound dressing can be designed to conform closely to the wound's contours, and it aids in monitoring changes in wound morphology over time. This component thus enhances the overall wound tissue classification and treatment planning by adding critical spatial context to the spectral data.

Digital fabrication file means a computer-generated file that contains the geometric design and material distribution instructions for manufacturing a custom object using digital fabrication equipment. In the context of this wound treatment system, the digital fabrication file defines the three-dimensional structure and composition of a patient-specific heterogeneous dressing to be produced by a three-dimensional printer. This file may be derived from the processed wound data, including the three-dimensional digital surface model and tissue classification results, to ensure that the designed dressing conforms to the wound's shape and addresses identified tissue conditions. The digital fabrication file typically includes parameters such as the dressing's dimensions, layer thicknesses, regions of different hydrogel matrices, and locations where various therapeutic compounds are to be deposited. It can be formatted in a standard 3D printing instruction language (for example, as a G-code script or an STL file with embedded material annotations) that is interpretable by the printer. By using the digital fabrication file, the system translates the wound analysis into concrete printing instructions, enabling automated fabrication of a wound dressing precisely tailored in size, topology, and functional composition for the wound. This file serves as a crucial link between the computational dressing design and its physical realization, ensuring reproducibility and accuracy in the dressing fabrication process.

Heterogeneous dressing means a wound dressing composed of multiple regions or layers that differ in material composition, structure, or therapeutic function across its extent. Rather than being uniform, a heterogeneous dressing provides varied properties in different areas so as to address the specific needs of corresponding wound tissue regions. In this invention, the heterogeneous dressing is custom-fabricated (for example, by a three-dimensional printer) based on the wound's geometry and tissue classification, resulting in a single dressing that integrates diverse components such as distinct hydrogel matrices or embedded therapeutic compounds in targeted locations. Each section of the dressing can be formulated to provide an optimal microenvironment or treatment for the underlying tissue: for instance, one area may incorporate an absorbent, antimicrobial hydrogel for an exuding, infected portion of the wound, while another area contains a hydrating, growth-factor-infused matrix to promote healing of a dry, granulating region. The dressing's heterogeneity ensures that care is spatially tailored, matching the varied conditions found within the wound, without requiring multiple separate dressings. The result is a contiguous wound covering that simultaneously delivers appropriate protection, moisture balance, and localized therapy to each part of the wound, as determined by the system's analysis of the wound's needs. This tailored approach ensures that each region of the wound receives the appropriate treatment within a single dressing application.

Hydrogel matrices means networked polymer gel structures that are highly absorbent and can retain a significant amount of water or biological fluids, often used in wound care for their moist healing environment and delivery of therapeutic agents. A hydrogel matrix is typically composed of cross-linked hydrophilic polymer chains (for example, alginate, collagen, or synthetic polymers) forming a three-dimensional scaffold that can swell with moisture. In the context of this invention, hydrogel matrices form key components of the custom wound dressing, providing a flexible and conformable medium that can be engineered with specific properties in different regions of the dressing. Multiple hydrogel matrices may be utilized or combined, each potentially loaded with different therapeutic compounds or having varying degrees of stiffness, porosity, or degradation rate, to suit the underlying tissue's requirements. For instance, one region of the dressing may use a hydrogel matrix infused with antibiotics to treat an area of infection, while another region uses a hydrogel optimized for high absorbency to manage heavy exudate. These hydrogel matrices not only maintain a moist wound interface conducive to healing but also serve as carriers for drugs or bioactive molecules, allowing controlled release at the wound site. Their inclusion in the heterogeneous dressing ensures close contact with the wound surface, cushioning the tissue and aiding tissue regeneration while addressing specific local conditions.

Image sensor means an electronic sensing device that captures optical images by converting light from a scene into digital signals. Common examples include charge-coupled devices (CCD) and complementary metal-oxide-semiconductor (CMOS) sensors as used in digital cameras. In this wound classification system, the image sensor is a part of the imaging apparatus and is positioned to capture images of the wound under various illumination conditions. It detects the intensity of light reflected or emitted from the wound at each pixel, thereby forming multispectral images when used in conjunction with controlled wavelength-specific illumination from the optical sources. The image sensor may operate in multiple spectral bands (for instance, encompassing visible and near-infrared wavelengths) either through multiple sensor units, filtering mechanisms, or sequential image capture under different lighting. The resolution and sensitivity of the image sensor are selected to ensure that fine details of wound tissue regions can be discerned and that subtle differences in optical reflectance are recorded for analysis. Data output from the image sensor forms the core of the multispectral dataset, providing the visual and spectral information needed by the classification algorithm to identify tissue types. The image sensor serves as the primary tool for acquiring detailed, quantitative image data of the wound's appearance across different wavelengths in the invention.

Imaging apparatus means the assembly of hardware configured to capture raw data from the wound, including visual and depth information, for subsequent analysis. In this invention, the imaging apparatus typically comprises at least one image sensor for capturing multispectral images of the wound, a depth sensor for measuring wound surface topology, and a set of optical sources for providing controlled, wavelength-specific illumination. These components are arranged and synchronized so that the wound can be imaged under various lighting conditions and from appropriate angles to gather comprehensive data without physical contact. The imaging apparatus may be a handheld or mounted device that houses the sensors and light emitters, possibly including optics (such as lenses or beam splitters) and calibration elements to ensure accurate co-registration of images and depth measurements. It is responsible for producing the multispectral dataset that reflects both the wound's appearance and its three-dimensional shape. The apparatus may be controlled by a computing unit or a user interface to initiate image capture sequences (for example, cycling through different colored lights and capturing corresponding images). By integrating multiple sensing modalities, the imaging apparatus of this system ensures that all necessary wound information-color, reflectance at different wavelengths, spatial dimensions, and thermal or other data if applicable—is collected in a consistent manner for analysis by the classification algorithm.

Machine-learning model means a computational model that has been trained on data to recognize patterns or make predictions, improving its performance without being explicitly programmed with fixed rules. Such a model often takes the form of an algorithmic structure (for example, a neural network, decision tree ensemble, or support vector machine) whose internal parameters are optimized by learning from a large set of example inputs and known outputs. In the context of this wound tissue classification system, the machine-learning model is developed using training data consisting of multispectral images (and possibly additional sensor inputs) of wounds where the tissue types or conditions in each region are known. Through this training process, the model learns to correlate specific features of the input data (such as spectral reflectance patterns, texture, and temperature gradients) with particular tissue types or healing states. Once trained, the machine-learning model is embedded in the classification algorithm to analyze new wound data and automatically classify wound tissue regions. It thereby enables the system to identify, for instance, regions of necrotic tissue versus granulation tissue based on complex data signatures that would be difficult to delineate with manual rules. The machine-learning model continuously applies its learned decision-making in a consistent manner, providing an objective and reproducible tissue classification result that underpins the wound assessment capabilities of the invention.

Multispectral dataset means the collection of image data and related sensor information captured across multiple portions of the electromagnetic spectrum for a given wound. This dataset is generated by the imaging apparatus and typically includes a set of multispectral images obtained under different wavelength-specific illumination conditions.

In the context of the present system, the multispectral dataset may also encompass additional aligned data modalities acquired during the same imaging session, such as depth measurements from the depth sensor, thermal imaging maps of the wound's temperature distribution, or even ultrasound data, thereby forming a comprehensive record of the wound's state. Each element of the dataset provides a different perspective: the various wavelength images reveal differences in tissue composition and blood perfusion, while the depth data contributes geometric context and the thermal or ultrasound data offer physiological insights. The multispectral dataset serves as the input to the classification algorithm, which processes this rich information to perform tissue classification. By preserving spatial correspondence between all its components (for example, each pixel location in the images maps to a specific coordinate on the wound via the depth model), the dataset allows the system to correlate spectral signals with exact wound locations. The multispectral dataset is the aggregated sensor output that encapsulates both the visual and structural characteristics of the wound necessary for analysis in this invention.

Multispectral images means a series of images of the same scene captured at different specific wavelengths or wavelength bands, providing information beyond the standard visible color range. Each image in a multispectral set corresponds to illumination or detection in a particular spectral band (for example, blue light, red light, near-infrared, etc.), so that when combined, these images reveal how the wound tissue reflects or absorbs light differently across the spectrum. In the context of this invention, multispectral images of a wound are taken using the imaging apparatus by sequentially activating various optical sources and recording the wound's appearance with the image sensor under each distinct wavelength-specific illumination. The result is a stack of aligned images where each layer highlights different aspects of tissue composition: for instance, certain wavelengths may accentuate blood oxygenation levels in tissue, while others highlight the presence of moisture or biofilm. These images are core components of the multispectral dataset and provide the raw visual data that the classification algorithm uses to distinguish between tissue types. By analyzing patterns across the multispectral images (such as relative brightness or color ratios at corresponding pixels), the system can detect subtle changes or features not apparent in ordinary white-light imaging, thereby improving the accuracy of wound tissue classification.

Optical reflectance means the portion or percentage of incident light that a surface (such as tissue) reflects back, as opposed to absorbing or transmitting. It is a fundamental optical property that can vary with the wavelength of light and with the material or tissue composition of the surface. In this wound assessment system, optical reflectance is measured by illuminating the wound with known wavelengths of light and capturing the intensity of the reflected light with the image sensor. Different wound tissue types exhibit distinct reflectance characteristics at various wavelengths—for example, oxygenated blood in healthy granulation tissue may reflect infrared light differently than denser, necrotic tissue or than surrounding skin with melanin. By recording optical reflectance in the form of pixel intensities in the multispectral images, the system obtains quantitative data about tissue properties. The classification algorithm uses these reflectance values as key features to differentiate tissue types, essentially interpreting how bright or dim each wound area appears under each wavelength. High or low reflectance at certain wavelengths can indicate specific conditions (such as the presence of moisture, level of perfusion, or amount of fibrotic tissue). Thus, optical reflectance provides the basis for spectral contrast in the multispectral dataset, enabling the photonic identification of different wound tissue regions in the invention.

Optical sources means the light-emitting elements used to illuminate the wound area with specific wavelengths of light during imaging. These sources can include light-emitting diodes (LEDs), laser diodes, or other lamps arranged in the imaging apparatus to provide controlled illumination across various spectral bands (for instance, visible colors like red or blue, and non-visible bands like near-infrared). The optical sources are typically selected or tuned to wavelengths that are useful for highlighting differences in tissue characteristics—for example, a certain wavelength may penetrate deeper or reveal blood oxygenation, while another may enhance contrast of superficial features. In operation, the system drives each optical source (or a subset of them) in a sequence, achieving wavelength-specific illumination of the wound which the image sensor then captures as multispectral images. The intensity and duration of each light emission can be controlled to ensure consistent lighting conditions and to avoid overheating or harming the tissue. Because of the multiple optical sources, the imaging apparatus can gather a multispectral dataset by effectively "shining" different colors of light on the wound and recording the reflected images. These optical sources thus enable the system to collect the necessary optical reflectance data across different wavelengths, forming an essential part of the multispectral photonic imaging approach used in this invention.

Skin tones means the range of natural pigmentation and coloration found in human skin, primarily determined by melanin content, that can affect the visual and optical characteristics of the skin and wounds. Different individuals have varying skin tones (from very light to very dark), which in the context of wound imaging may influence the baseline reflectance values and contrast in captured images. In this invention, consideration of skin tones is important because the imaging apparatus may capture not only the wound itself but also the surrounding skin as a reference or boundary. The classification algorithm and machine-learning model are preferably trained or calibrated to account for different skin tones, ensuring that tissue classification remains accurate across diverse patient populations. For instance, melanin strongly absorbs certain wavelengths (like blue light), which could make a wound on darker skin appear differently than on lighter skin under the same illumination; the system compensates for such differences either through normalization techniques or through robust feature selection. Thus, "skin tones" in the context of the system refers to the variable background and patient-specific optical properties that the system must accommodate. By addressing the effects of various skin tones, the invention maintains consistent performance in identifying wound tissue regions without bias or loss of accuracy due to skin color differences. In traditional imaging systems (for example, standard RGB photography or basic digital wound cameras), accommodating a broad range of skin pigmentation has proven difficult, wounds on darkly pigmented skin often exhibit lower contrast and can confound color-based tissue assessment, while those same algorithms may over-emphasize certain hues on light skin. The present multispectral approach mitigates these issues by extending analysis beyond the visible spectrum and by applying calibrated normalization. The system captures reflectance in spectral bands less affected by melanin (such as certain near-infrared wavelengths), ensuring that underlying tissue features are visible even when melanin content is high. Additionally, the classification algorithm in this invention actively normalizes image data against the patient's surrounding skin baseline, effectively adjusting for melanin-induced intensity differ- ences before applying tissue classification thresholds. Fur- thermore, the machine-learning model is trained on a diverse dataset of wound images spanning a wide variety of skin tones, so that it learns features invariant to skin pigmenta- tion. By incorporating data from patients with very light to very dark skin during training, the algorithm develops a robustness to melanin variation that previous systems lack- ing such training could not achieve. Collectively, these measures enable the system to perform accurate wound tissue classification across all skin tones, where prior imag- ing techniques would struggle with consistency and accu- racy due to the optical interference of varying melanin levels.

Spatial coordinate-specific tissue conditions means the localized state or characteristics of wound tissue as identi- fied at particular positions (coordinates) on the wound's surface. Essentially, the term refers to information about the wound's tissue health or type that is tied to a specific location within the wound area. In this invention, after the imaging data is analyzed, the system determines various tissue conditions (for example, whether the tissue at a certain point is necrotic, infected, granulating, or epithelializing) and associates each determination with a corresponding spatial coordinate on the wound (often derived from the three-dimensional digital surface model). These spatially resolved tissue descriptors allow the wound to be mapped in terms of its varying conditions, producing a detailed profile of what is happening at each part of the wound. For instance, one coordinate on the map may be labeled as having a high level of moisture and slough tissue, while another coordinate is identified as dry granulation tissue. By using spatial coordinate-specific tissue conditions, the system can design targeted interventions—the heterogeneous dressing, for example, is configured based on this map, placing appro- priate materials or treatments at the exact coordinates where they are needed. This term underscores that the wound assessment is not just overall or averaged but finely resolved to the level of individual points or regions on the wound surface, as facilitated by the invention's precise imaging and analysis.

Structured-light means a three-dimensional imaging tech- nique in which a known pattern of light (such as grids, stripes, or dots) is projected onto a surface and observed by a camera to deduce the surface's shape from the way the pattern deforms. In practice, the system projects this struc- tured illumination onto the wound and the image sensor captures the distorted pattern. By analyzing these distortions using computational algorithms, the depth and contour information of the wound surface can be calculated. In the context of this invention, structured-light is one method employed by the depth sensor or imaging apparatus to obtain the three-dimensional digital surface model of the wound. It enables accurate mapping of wound geometry, including variations in depth and the presence of any irregular topog- raphy, without physically contacting the wound. The struc- tured-light approach can be particularly useful for capturing fine details in wound morphology by using high-resolution pattern projection and analysis. As part of the imaging process, it may be used alone or in combination with other ranging methods (like time-of-flight) to improve the robust- ness of depth measurements. Ultimately, the structured-light technique provides precise spatial data that complements the multispectral images, ensuring that the system has both spectral and geometrical information for each portion of the wound for comprehensive tissue classification and dressing design.

Therapeutic compounds means chemical or biological agents that provide a therapeutic effect to promote wound healing or treat wound-related conditions when applied to the tissue. These compounds can include a wide range of substances such as antimicrobials (e.g., antibiotics or silver ions to reduce infection), anti-inflammatory agents, analge- sics (pain relievers), growth factors (to stimulate tissue regeneration), enzymes (to debride necrotic tissue), or other medications relevant to wound care. In the context of this invention, therapeutic compounds are incorporated into the heterogeneous wound dressing in targeted locations as deter- mined by the wound's specific needs. For example, if the classification algorithm identifies a region of the wound with signs of bacterial infection, the dressing section correspond- ing to that region can be loaded with an antibacterial compound; similarly, a zone of stalled healing might receive a compound like a growth factor or collagen to encourage tissue repair. These compounds are often embedded within or bound to hydrogel matrices or other dressing materials so that they can be gradually released into the wound over time. By strategically placing therapeutic compounds throughout the custom-fabricated dressing, the system provides local- ized treatment, ensuring that each wound tissue region receives the appropriate therapeutic intervention as part of the dressing application, in accordance with the invention's treatment strategy.

Thermal imaging means the capture of infrared radiation from objects to create an image representing temperature distribution across the observed scene. Since all objects with temperature above absolute zero emit infrared radiation, a thermal imaging device (such as an infrared camera) can detect the emitted energy from the wound and surrounding tissue to produce a heat map where different colors or intensity levels correspond to different temperatures. In the context of this wound classification system, thermal imaging provides complementary information about the wound's physiological state: areas of increased warmth may indicate infection or inflammation due to higher blood flow, whereas cooler areas might suggest poor circulation or devitalized tissue. The imaging apparatus may include a thermal sensor or camera to record the wound's thermal profile concur- rently with the multispectral optical images. The resulting thermal data can be integrated into the multispectral dataset, aligning with the visual images and depth information for analysis. The classification algorithm can consider tempera- ture variations as one of the features when identifying tissue conditions, thereby improving the accuracy of detecting, for instance, an infected region that is hotter than its surround- ings. Thermal imaging is thus a non-contact diagnostic modality included in the invention to enhance wound assess- ment by revealing underlying metabolic or circulatory aspects of the wound that are not visible in standard optical images.

Three-dimensional digital surface model means a repre- sentation of the shape and topography of a surface in three-dimensional space, stored and manipulated in digital form. It typically consists of a set of coordinates (and possibly a mesh of connected triangles or a grid) that model the geometry of the surface—in this case, the external contours of a wound and possibly its immediate surrounding skin. In the context of this invention, the three-dimensional digital surface model of the wound is generated from data captured by the depth sensor (using techniques such as structured-light or time-of-flight measurements) combined with spatial registration from the image sensor. This model accurately captures features such as the depth at each point of the wound, the slope of the wound edges, and the wound's overall volume and area. The digital surface model serves multiple purposes in the system: it allows precise mapping of identified tissue classifications onto the wound's geometry by linking each wound tissue region to specific coordinates and depths, and it provides the basis for designing a conformal wound dressing. During the dressing design process, the model is used to ensure that the shape of the heterogeneous dressing will match the wound's surface profile so that it fits snugly and contacts all areas of the wound. Additionally, the three-dimensional digital surface model can be saved and compared over time to monitor changes in wound size or depth, making it a valuable representation for treatment planning and long-term monitoring of wound healing.

Three-dimensional printer means an additive manufacturing device that builds three-dimensional objects layer by layer from a digital design file. Often referred to simply as a 3D printer, this machine typically works by extruding or solidifying material (such as plastic, resin, or in this case biocompatible hydrogel and other compounds) under computer control to form a desired shape. In the context of the invention, the three-dimensional printer is used to fabricate the custom heterogeneous wound dressing as specified by the digital fabrication file. It reads the instructions detailing the dressing's geometry and composition and then deposits the materials accordingly, creating the physical dressing that matches the wound's dimensions and varies in content across different regions. For example, the printer may have multiple print heads or nozzles to dispense different hydrogel formulations or therapeutic compounds at precise locations corresponding to the design. The printing process can build up the dressing in layers, ensuring features like thickness gradients or embedded medication reservoirs are accurately formed. The three-dimensional printer operates under sterile or controlled conditions suitable for producing medical-grade dressings. The result of its operation is a patient-specific wound dressing that emerges directly from the digital plan to a tangible product, illustrating how the system translates computational analysis into a manufactured therapeutic device. This printer is thus a key component in realizing the personalized treatment strategy of the invention, enabling on-demand creation of dressings tailored to an individual wound.

Time-of-flight means a distance measurement principle (and related sensor technology) based on the time taken by a wave-typically a pulse of light or sound—to travel to a target and back to the detector. By knowing the speed of the wave (for instance, the speed of light) and measuring the round-trip travel time, the distance to the target can be calculated. In the context of this invention, time-of-flight is used in a depth sensor (such as a time-of-flight camera or LIDAR module) to rapidly capture the three-dimensional profile of the wound. The depth sensor emits brief light pulses toward the wound and records the time it takes for each pulse to reflect off the wound surface and return. Each pixel in a time-of-flight camera, for example, can independently measure the distance to the corresponding point on the wound, producing a depth map of the entire scene in real time. This method allows the system to obtain accurate wound measurements (like depth and contour) efficiently and without contact. Time-of-flight data contributes to the creation of the three-dimensional digital surface model, complementing or providing an alternative to structured-light techniques. Its advantage in the wound classification system is the ability to quickly gather spatial information even in conditions with varying ambient light, thereby enhancing the robustness of the imaging apparatus. Overall, time-of-flight sensing ensures that detailed geometric information about the wound is available for analysis and custom dressing fabrication in the invention.

Tissue classification means the process of identifying and categorizing the types or conditions of biological tissue present in a given area based on observed data. In this invention, tissue classification refers specifically to determining what kinds of tissue are present in different parts of a wound (for example, distinguishing necrotic tissue, granulation tissue, epithelial tissue, etc.) by analyzing the wound's multispectral images and other sensor inputs. This classification is typically performed by the system's algorithm (which may utilize a machine-learning model) using features such as color, optical reflectance at various wavelengths, temperature, and texture. The result of tissue classification is an output that labels sections of the wound with their respective tissue type or condition, effectively segmenting the wound into meaningful regions. Such a classification is crucial in wound care, as different tissue types indicate different stages of healing or require different treatments—for instance, identifying areas of necrosis might signal the need for debridement, while recognizing healthy granulation tissue can confirm healing progress. In the context of the claims, tissue classification provides the information needed to guide subsequent steps like the design of a heterogeneous dressing tailored to the wound. It ensures that the system can objectively characterize the wound's status in a reproducible manner, forming a basis for personalized therapy decisions in the invention.

Tissue types means distinct categories of biological tissue characterized by specific structure or pathological condition, especially as they relate to the composition of a wound. Examples of tissue types relevant to wound assessment include but are not limited to: healthy epithelial tissue (skin), granulation tissue (new connective tissue and microscopic blood vessels indicating healing), necrotic tissue (dead or devitalized tissue, often black or yellow in appearance such as eschar or slough), subcutaneous fat, muscle tissue, or other identifiable components in the wound bed. In the context of this invention, the term "tissue types" refers to the classifications that the system's algorithm aims to distinguish within the wound. The multispectral imaging and analysis can differentiate these tissue types by detecting their unique signatures (for instance, differences in optical reflectance, color, and temperature). By identifying various tissue types present in wound tissue regions, the system can provide a detailed description of the wound's composition. This information is used to tailor treatment: for example, knowing that both necrotic and granulating tissue types are present, the clinician or the automated system can plan for both debridement and support of healing tissue. Thus, "tissue types" encapsulates the different kinds of tissue that the wound classification system must recognize and address when analyzing and treating a wound.

Ultrasound data means information obtained from an ultrasound imaging modality, which uses high-frequency sound waves to visualize or assess internal features of tissues. Ultrasound devices emit sound pulses and record the echoes that return from tissue boundaries or density changes, producing data that can be rendered as images or quantitative measurements of depth and structure. In this invention, ultrasound data may be included as part of the wound assessment to provide insight beneath the visible surface of the wound. For instance, an ultrasound scan of a wound can reveal the thickness of tissue layers, the presence of fluid pockets or underlying blood flow (via Doppler ultrasound), or the condition of tissue beneath a scab or eschar. Such data can complement the optical and thermal information by confirming how deep a wound extends or whether there are hidden complications like abscesses. If the system integrates an ultrasound probe or receives ultrasound data, this information becomes part of the multispectral dataset, aligned with the surface map of the wound. The classification algorithm can incorporate ultrasound-derived features (for example, distinguishing tissue consistency or detecting undermining of wound edges) to refine the tissue classification. Ultrasound data in the context of the system provides an additional layer of diagnostic detail, enhancing the understanding of the wound's condition beyond what is visible externally, and thereby supporting more informed treatment design.

Wavelength-specific illumination means the deliberate use of light at particular wavelengths (or narrow wavelength bands) to illuminate a target, rather than using broad-spectrum or white light. By selecting specific wavelengths for illumination, one can highlight or isolate certain optical characteristics of the target. In this system, wavelength-specific illumination is employed by the optical sources of the imaging apparatus to sequentially bathe the wound in different colors or spectral bands of light (for example, blue, green, red, near-infrared, etc.). Each such illumination causes the wound tissue to reflect light in that band, which is then captured as an image by the sensor. Because different tissue components and conditions respond uniquely to different wavelengths—for instance, blood and oxygenated tissue might reflect infrared light differently than they do green light-using wavelength-specific illumination allows the collection of multispectral images that contain diagnostic spectral information. This approach is fundamental to multispectral photonic analysis, as it provides controlled conditions to measure optical reflectance at known wavelengths. The term underscores that the system's imaging is not passive but actively controlled: the illumination is tuned to specific wavelengths that are chosen for their relevance to tissue differentiation. Consequently, wavelength-specific illumination enables the identification of subtle variations in wound tissue that would not be apparent under normal light, thereby supporting the accurate tissue classification capabilities of the invention.

Wound means an area of tissue that has been opened, damaged, or broken due to injury, surgery, burn, ulceration, or other causes, which triggers a healing process. A wound typically involves a disruption of the skin and possibly underlying tissues, and it can include various tissue types such as exposed flesh, necrotic (dead) tissue, granulation tissue forming during healing, and intact skin at the margins. In the context of this invention, a wound is the subject being imaged and analyzed; it can be of acute nature (like a surgical incision or laceration) or chronic nature (like a diabetic ulcer or pressure injury). Wounds often present irregular shapes, depths, and a mixture of healthy and unhealthy tissue regions, which complicates assessment and treatment. The present system is designed to assess such wounds by capturing multispectral images and other data to identify the composition and condition of the wound. The term "wound" as used in the claims encompasses any break in the integument (skin) or organ surface that is being evaluated or treated. Accurately characterizing the wound— in terms of its boundaries, area, and internal tissue makeup—is essential for guiding interventions such as applying an appropriate wound dressing. Therefore, in this specification, a wound broadly refers to the physical lesion or ulcer that the multispectral photonic classification system is intended to evaluate and help heal. The system can accommodate various clinical wound healing processes, including wounds healing by primary intention, secondary intention, and tertiary intention. Primary intention healing refers to wounds that are closed immediately and directly, typically with sutures, staples, or adhesive, such as a clean surgical incision where the wound edges are approximated. In these cases, minimal new tissue needs to form, and healing is rapid; the system's imaging and dressing fabrication focus on ensuring the custom dressing protects the closed wound, maintains a sterile environment, and supports the swift epithelialization and minimal scarring expected with primary closure. Secondary intention healing occurs in wounds left open to heal naturally from the bottom upward, as is common in large trauma wounds, chronic ulcers, or other wounds with significant tissue loss that cannot be sutured. For such wounds, the system's multispectral imaging continuously monitors the development of granulation tissue and contraction of the wound over time. The generated dressings are designed to conform to an open wound bed and are adjusted over successive applications to manage exudate, promote moist wound healing, and encourage tissue granulation, addressing the longer, staged healing process inherent to secondary intention. Tertiary intention (delayed primary closure) involves initially treating a wound as an open wound (similar to secondary intention) to allow for cleaning or infection control and then subsequently closing the wound at a later stage. An example is a contaminated abdominal wound left open for several days and then surgically closed once clean. In such scenarios, the system adapts by first providing a custom dressing for the initial open-wound period that might incorporate antimicrobial agents and absorptive materials to reduce bioburden and prepare the wound bed; subsequently, after the wound is closed by sutures or other means, the system can generate a second-stage dressing optimized for the post-closure healing (for instance, focusing on protecting the sutured site and supporting final tissue integration). Thus, the multispectral imaging and dressing fabrication process of this invention is versatile across all three healing intentions, whether it's a neatly closed surgical incision, a large open ulcer healing gradually, or a wound managed with delayed closure, ensuring that each type of wound benefits from a tailored assessment and a sequence of customized therapeutic dressings suited to its specific healing pathway.

Wound dressing means a material or medical device applied to cover and protect a wound, often with the purpose of promoting healing, maintaining a controlled environment (such as moisture balance), and preventing contamination. Traditional wound dressings include gauze, bandages, hydrocolloid pads, and hydrogel sheets, which serve to keep the wound clean and can deliver medications or absorb exudate. In the context of this invention, the wound dressing specifically refers to the custom-fabricated, heterogeneous dressing produced by the system's three-dimensional printer according to the design derived from the wound analysis. This dressing is tailored to the wound's geometry and needs, meaning it is shaped to fit the wound and contains region-specific features (for example, varying thickness or embedded therapeutic compounds) corresponding to the underlying wound tissue regions. The wound dressing thus created by the system is intended to cover the wound completely, adhering or conforming to the wound bed and margins. It provides a protective barrier while also actively engaging with the wound-keeping it appropriately moist, delivering drugs (such as antibiotics or growth factors), and absorbing excess fluids where necessary. Within this specification, a wound dressing is not just any bandage, but in particular the outcome of the inventive process: a patient-specific, multi- functional covering designed to optimize healing for the wound being treated.

Wound tissue regions means distinct portions or segments of a wound that are identified based on the type or condition of tissue they contain. Because a single wound can encompass multiple tissue states (for example, areas of necrosis, areas of active granulation, and areas of re-epithelialization), it is useful to conceptually divide the wound into regions, each characterized by relatively uniform tissue features. In this invention, wound tissue regions are determined by the analysis of the multispectral dataset: the classification algorithm segments the wound and labels each segment according to its tissue type or condition. Each wound tissue region corresponds to a specific location on the wound (often delineated in the three-dimensional digital surface model) and is associated with the classification output, such as "necrotic region," "granulation region," or "intact skin margin." Identifying these wound tissue regions allows the system to target interventions precisely—for instance, by designing the heterogeneous dressing so that each region of the dressing aligns with and addresses the needs of the corresponding region of the wound. In the claims and specification, this term emphasizes that the wound is not treated as a uniform entity but rather as a collection of different regional tissue environments, each of which can be individually assessed and managed. The concept of wound tissue regions is fundamental to the tailored approach of the multispectral photonic classification system, ensuring that diverse tissue conditions within a wound are recognized and catered to in the treatment plan.

In the aforementioned detailed description of the present invention, reference is made to the accompanying drawings, which form a part thereof, and within which are shown by way of illustration specific embodiments by which the invention may be practiced. Numerous specific details are set forth to provide a thorough description of the embodiments of the present invention. It will be apparent to one of ordinary skill in the art that some embodiments may be practiced without some of these specific details. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

All numerical designations, such as measurements, efficacies, physical characteristics, forces, and other designations, including ranges, are approximations which are varied up or down by increments of 1.0 or 0.1, as appropriate. It is to be understood, even if it is not always explicitly stated that all numerical designations are preceded by the term "approximately." As used herein, "approximately" refers to being within an acceptable error range for the particular value as determined by one of ordinary skill in the art, which will depend in part on how the value is measured or determined. When an acceptable range is not dictated by the one of ordinary skill in the art, "approximately" refers to ±15% of the numerical when used in connection with particular values; it should be understood that a numerical including an associated range with a lower boundary of greater than zero must be a non-zero numerical, and the term "approximately" should be understood to include only non-zero values in such scenarios.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for classifying wound tissue and generating a customized therapeutic wound dressing, comprising:

a. illuminating a wound on a subject with an imaging apparatus comprising a plurality of distinct wavelength-specific optical sources configured to sequentially or simultaneously emit electromagnetic radiation at predetermined optical wavelengths onto the wound;

b. capturing, with an image sensor integrated within the imaging apparatus and spatially aligned with the optical sources, a plurality of multispectral images corresponding respectively to the predetermined optical wavelengths, thereby generating a tangible multispectral dataset representing reflectance intensities of the wound tissue at each of the predetermined optical wavelengths;

c. computationally processing the tangible multispectral dataset by applying a trained machine-learning classification algorithm stored in non-transitory computer-readable memory to identify and spatially classify at least two distinct tissue types within the wound based on differences in optical reflectance properties at the predetermined optical wavelengths, thereby generating a wound tissue classification map comprising spatially delineated wound tissue regions;

d. generating, using depth data obtained from a depth sensor integrated within the imaging apparatus and spatially calibrated to the image sensor, a three-dimensional digital surface model of the wound, wherein the depth sensor employs a structured-light or time-of-flight optical measurement to obtain spatial geometry data of the wound;

e. automatically designing, using a processor and based on the generated wound tissue classification map and the three-dimensional digital surface model of the wound, a digital fabrication file comprising instructions executable by a three-dimensional printer, the digital fabrication file defining a patient-specific wound dressing having a geometry conforming to the spatial geometry and tissue-type distribution of the wound, wherein the geometry of the patient-specific wound dressing varies in at least one physical or chemical property based upon the identified tissue types at corresponding spatial locations, the at least one physical or chemical property comprising a spatial distribution of therapeutic compound identity and/or therapeutic compound concentration across multiple heterogeneous regions of a single fabricated dressing, and wherein the digital fabrication file encodes region-wise material deposition instructions and/or therapeutic compound dosing instructions comprising at least one of multi-material toolpaths or multi-dosing toolpaths aligned to the wound tissue classification map, and wherein the digital fabrication file further encodes (i) cutting instructions for cutting at least one sheet material layer of the patient-specific wound dressing and (ii) fiducial-based registration data mapping the wound tissue classification map to a printer coordinate system; and f. transmitting the digital fabrication file to a computer-controlled three-dimensional printing device, causing the device to fabricate the patient-specific wound dressing as a tangible medical therapeutic product having physical geometry and properties customized to the spatial geometry and tissue classification of the wound, including fabrication of the multiple heterogeneous regions of the single fabricated dressing according to the encoded region-wise material deposition instructions and/or therapeutic compound dosing instructions, wherein the three-dimensional printing device comprises a hybrid fabrication unit including (i) a cutting module configured to execute the cutting instructions to cut the at least one sheet material layer and (ii) a multi-material deposition module configured to deposit the multiple heterogeneous regions onto the at least one sheet material layer by executing the region-wise material deposition instructions and/or therapeutic compound dosing instructions, and wherein the hybrid fabrication unit includes an assembly pallet with fiducial markers detectable by a vision system to align the multi-material deposition module using the fiducial-based registration data.

2. The method of claim 1, wherein the plurality of distinct wavelength-specific optical sources comprise light-emitting diodes (LEDs) emitting optical wavelengths in visible and infrared spectra.

3. The method of claim 1, wherein the trained machine-learning classification algorithm comprises a convolutional neural network trained on labeled wound tissue datasets.

4. The method of claim 1, further comprising capturing thermal imaging data using an infrared thermal sensor integrated with the imaging apparatus, wherein computationally processing further includes integrating thermal imaging data to enhance tissue classification accuracy.

5. The method of claim 1, further comprising obtaining ultrasound imaging data from an ultrasound transducer integrated with or coupled to the imaging apparatus, and integrating the ultrasound imaging data into the three-dimensional digital surface model to improve spatial accuracy of sub-surface tissue characterization.

6. The method of claim 1, wherein computationally processing includes determining baseline skin pigmentation from tissue adjacent to the wound to adjust classification thresholds dynamically for varying skin tones.

7. The method of claim 1, wherein the patient-specific wound dressing includes regions specifically fabricated with antimicrobial materials positioned directly over tissue regions classified as necrotic.

8. The method of claim 1, wherein the patient-specific wound dressing comprises a top backing layer configured to secure the patient-specific wound dressing to surrounding skin, and multiple heterogeneous regions each having distinct therapeutic compounds selected specifically to correspond to the classified tissue type beneath each respective region, wherein the multiple heterogeneous regions comprise a first intermediate region, a second intermediate region laterally adjacent to the first intermediate region, and a deep filler plug extending from a wound-contact side of the patient-specific wound dressing into a wound cavity identified in the three-dimensional digital surface model.

9. The method of claim 8, wherein the distinct therapeutic compounds include antimicrobial agents, analgesics, collagen scaffolds, hydrogel matrices, anti-inflammatory agents, growth factors, or enzymatic debridement agents.

10. The method of claim 8, wherein the therapeutic compounds are localized in specific vertical layers of the patient-specific wound dressing based on the depth of the identified tissue types within the wound, including localizing at least one therapeutic compound within the deep filler plug to contact a wound base identified in the three-dimensional digital surface model.

11. The method of claim 8, wherein the therapeutic compounds vary laterally across the dressing to correspond with classified tissue types identified at corresponding spatial coordinates in the wound.

12. The method of claim 1, wherein the subject is a non-human animal, and the imaging apparatus includes calibration specific to the optical properties of the non-human animal's skin or fur.

13. A system for multispectral wound tissue classification and customized dressing fabrication, comprising:

a. an imaging apparatus comprising:
   i. a plurality of wavelength-specific optical emitters configured to illuminate a wound;
   ii. at least one image sensor spatially aligned with the optical emitters to capture multispectral images;
   iii. a depth sensor providing three-dimensional spatial data of the wound;

b. a processing unit comprising at least one processor and non-transitory computer-readable memory storing instructions configured to cause the at least one processor to:
   i. process multispectral image data and depth data;
   ii. classify wound tissue types using stored machine-learning algorithms to generate a wound tissue classification map;
   iii. generate a three-dimensional wound surface model;
   iv. create a digital fabrication file defining a customized dressing matching the wound surface and tissue classifications, including heterogeneous therapeutic regions selected based on the classified tissue types, wherein the customized dressing varies in at least one physical or chemical property comprising a spatial distribution of therapeutic compound identity and/or therapeutic compound concentration across multiple heterogeneous regions of a single fabricated dressing, and wherein the digital fabrication file encodes region-wise material deposition instructions and/or therapeutic compound dosing instructions comprising at least one of multi-material toolpaths or multi-dosing toolpaths aligned to the wound tissue classification map, and wherein the digital fabrication file further encodes (i) cutting instructions for cutting at least one sheet material layer of the customized dressing and (ii) fiducial-based registration data mapping the wound tissue classification map to a printer coordinate system; and c. a computer-controlled three-dimensional printer configured to fabricate the customized dressing based on the digital fabrication file, wherein the three-dimensional printer comprises a hybrid fabrication unit including (i) a cutting module configured to execute the cutting instructions to cut the at least one sheet material layer and (ii) a multi-material deposition module configured to deposit the heterogeneous therapeutic regions onto the at least one sheet material layer by executing the region-wise material deposition instructions and/or therapeutic compound dosing instructions, and wherein the hybrid fabrication unit includes an assembly pallet with fiducial markers detectable by a vision system to align the multi-material deposition module using the fiducial-based registration data.

14. The system of claim 13, further comprising an infrared thermal imaging sensor integrated with the imaging apparatus and coupled to the processing unit.

15. The system of claim 13, further comprising an ultrasound transducer operatively coupled to the processing unit to provide subsurface wound characterization data.

16. The system of claim 13, wherein the customized dressing comprises distinct therapeutic regions fabricated from antimicrobial, analgesic, collagen scaffold, or hydrogel materials based on the underlying classified tissue type.

17. A non-transitory computer-readable medium storing instructions executable by a processor, configured to cause a system to perform a method comprising:
   a. receiving multispectral image data captured from a wound illuminated at multiple predetermined optical wavelengths;
   b. classifying tissue types within the wound using trained machine-learning models based on reflectance characteristics, thereby generating a wound tissue classification map that delineates spatial regions of different tissue types in the wound;
   c. generating a three-dimensional model of the wound surface from depth sensor data;
   d. automatically designing a digital fabrication file for a customized wound dressing based on the tissue classifications and the three-dimensional model, wherein the customized wound dressing includes heterogeneous regions having therapeutic compounds specifically aligned with the classified tissue types, the heterogeneous regions providing a spatial distribution of therapeutic compound identity and/or therapeutic compound concentration across multiple heterogeneous regions of a single fabricated dressing, and wherein the digital fabrication file encodes region-wise material deposition instructions and/or therapeutic compound dosing instructions comprising at least one of multi-material toolpaths or multi-dosing toolpaths aligned to the wound tissue classification map, and wherein the digital fabrication file further encodes (i) cutting instructions for cutting at least one sheet material layer of the customized wound dressing and (ii) fiducial-based registration data mapping the wound tissue classification map to a printer coordinate system; and
   e. transmitting the digital fabrication file to a three-dimensional printer to fabricate a tangible customized therapeutic wound dressing, wherein the three-dimensional printer comprises a hybrid fabrication unit including (i) a cutting module configured to execute the cutting instructions to cut the at least one sheet material layer and (ii) a multi-material deposition module configured to deposit the heterogeneous regions onto the at least one sheet material layer by executing the region-wise material deposition instructions and/or therapeutic compound dosing instructions, and wherein the hybrid fabrication unit includes an assembly pallet with fiducial markers detectable by a vision system to align the multi-material deposition module using the fiducial-based registration data.

18. The non-transitory computer-readable medium of claim 17, further comprising instructions to integrate thermal imaging data into the tissue classification process.

19. The non-transitory computer-readable medium of claim 17, further comprising instructions to integrate ultrasound data into the three-dimensional wound model.

20. The non-transitory computer-readable medium of claim 17, wherein the therapeutic compounds include antimicrobial agents, analgesics, collagen scaffolds, hydrogel matrices, anti-inflammatory agents, growth factors, or enzymatic debridement agents localized in specific regions based on wound tissue classification.

21. A system for multispectral wound tissue classification and time-sequenced customized dressing fabrication, comprising:
   a. an imaging apparatus comprising:
      i. a plurality of distinct wavelength-specific optical emitters configured to illuminate a wound;
      ii. at least one image sensor spatially aligned with the optical emitters to capture multispectral images of the wound;
      iii. a depth sensor calibrated with the image sensor to provide three-dimensional spatial data of the wound;
   b. a processing unit comprising at least one processor and a non-transitory computer-readable memory storing instructions configured to cause the at least one processor to:
      i. preprocess the multispectral image data and depth data captured from the wound by at least one of calibration, reflectance normalization, spatial registration, noise filtering, or artifact correction to generate preprocessed data;
      ii. classify wound tissue types by applying a trained machine-learning algorithm to the preprocessed data, thereby generating a wound tissue classification map that delineates spatial regions of different tissue types in the wound;
      iii. generate a three-dimensional digital surface model of the wound from the depth data, the model representing the wound's topography and dimensions;
      iv. create a first digital fabrication file defining a patient-specific customized three-dimensional wound dressing corresponding to a current state of the wound, the first digital fabrication file specifying a geometry conforming to the wound's surface and including heterogeneous regions with physical or chemical properties selected based on the classified tissue types at corresponding locations, wherein the physical or chemical properties comprise a spatial distribution of therapeutic compound identity and/or therapeutic compound concentration across multiple heterogeneous regions of a single fabricated dressing, and wherein the first digital fabrication file encodes region-wise material deposition instructions and/or therapeutic compound dosing instructions comprising at least one of multi-material toolpaths or multi-dosing toolpaths aligned to the wound tissue classification map, and wherein the first digital fabrication file further encodes (i) cutting instructions for cutting at least one sheet material layer of the patient-specific customized three-dimensional wound dressing and (ii) fiducial-based registration data mapping the wound tissue classification map to a printer coordinate system;

v. predict a wound healing progression using a multi-stage predictive wound model based on the wound tissue classification map and the three-dimensional digital surface model, thereby determining at least one anticipated future wound state comprising a predicted distribution of tissue types and wound geometry at a future time; and vi. create at least one additional digital fabrication file defining at least one future-stage custom wound dressing for the anticipated future wound state, the at least one future-stage custom wound dressing having a geometry and material composition modified according to the predicted changes in the wound, wherein the at least one additional digital fabrication file encodes region-wise material deposition instructions and/or therapeutic compound dosing instructions comprising at least one of multi-material toolpaths or multi-dosing toolpaths aligned to the predicted distribution of tissue types for the anticipated future wound state, and wherein the at least one additional digital fabrication file further encodes (i) cutting instructions for cutting at least one sheet material layer of the at least one future-stage custom wound dressing and (ii) fiducial-based registration data mapping the predicted distribution of tissue types to the printer coordinate system; and c. a computer-controlled three-dimensional printer configured to fabricate the patient-specific customized three-dimensional wound dressing and the at least one future-stage custom wound dressing based on the respective digital fabrication files, wherein the three-dimensional printer comprises a hybrid fabrication unit including (i) a cutting module configured to execute respective cutting instructions to cut at least one respective sheet material layer for each of the patient-specific customized three-dimensional wound dressing and the at least one future-stage custom wound dressing and (ii) a multi-material deposition module configured to deposit the heterogeneous regions onto the respective sheet material layers by executing respective region-wise material deposition instructions and/or therapeutic compound dosing instructions, and wherein the hybrid fabrication unit includes an assembly pallet with fiducial markers detectable by a vision system to align the multi-material deposition module using respective fiducial-based registration data.

22. The system of claim 21, wherein a first customized dressing corresponding to an initial wound state is fabricated with a hydrogel-based material, and wherein a subsequent customized dressing corresponding to a later wound state is fabricated with a gauze-based or fibrous material, thereby providing a staged transition in dressing material as the wound progresses from a high-moisture, early phase to a later phase requiring more absorptive or breathable dressing structure.

23. The system of claim 21, wherein a first customized dressing in the sequence contains an antimicrobial therapeutic compound targeting infection in the wound, and wherein a subsequent customized dressing contains a different therapeutic compound selected from analgesic agents or tissue-regeneration promoters, such that the embedded therapeutic compounds transition from infection control in an earlier stage to pain management or tissue growth support in a later healing stage.

24. The system of claim 21, wherein the processing unit includes a multi-stage predictive wound healing model configured to simulate changes in wound tissue composition and geometry over time, the model being trained on time-series wound data to output the anticipated future wound state based on the current wound state's data.

25. The system of claim 24, wherein the wound healing progression model comprises a temporal convolutional neural network trained on sequential wound images and three-dimensional wound models, the network being operative to analyze the wound's current multispectral image and depth data in context of learned healing patterns to predict the wound's future state.

26. The system of claim 24, wherein the wound healing progression model comprises a transformer-based machine learning model trained on voxelized volumetric representations of wounds captured at multiple time points, the model being configured to generate a predicted wound state by processing the wound's current three-dimensional data with attention mechanisms that account for learned temporal progression features.

27. The system of claim 21, wherein the processing unit is further configured to receive updated wound image data at one or more later times and to recalibrate or update the predicted future wound state based on actual healing progress, thereby adjusting at least one subsequently generated custom dressing design to more accurately reflect the wound's healing trajectory in the event that the wound deviates from the initially anticipated progression.

* * * * *